United States Patent
Fury et al.

(10) Patent No.: US 11,845,930 B2
(45) Date of Patent: Dec. 19, 2023

(54) METHODS AND SYSTEMS FOR CRISPR SELECTION

(71) Applicant: Regeneron Pharmaceuticals Inc., Tarrytown, NY (US)

(72) Inventors: Wen Fury, Tarrytown, NY (US); Yu Bai, Tarrytown, NY (US)

(73) Assignee: Regeneron Pharmaceuticals Inc., Tarrytown, NY (US)

( * ) Notice: Subject to any disclaimer, the term of this patent is extended or adjusted under 35 U.S.C. 154(b) by 875 days.

(21) Appl. No.: 16/821,607

(22) Filed: Mar. 17, 2020

(65) Prior Publication Data

US 2020/0299679 A1 Sep. 24, 2020

Related U.S. Application Data

(60) Provisional application No. 62/820,106, filed on Mar. 18, 2019.

(51) Int. Cl.
| | |
|---|---|
| *C12N 15/10* | (2006.01) |
| *G16B 20/00* | (2019.01) |
| *G16B 30/00* | (2019.01) |
| *C12Q 1/6874* | (2018.01) |
| *G16B 25/00* | (2019.01) |
| *G01N 33/50* | (2006.01) |

(52) U.S. Cl.
CPC ....... *C12N 15/1079* (2013.01); *C12Q 1/6874* (2013.01); *G01N 33/5008* (2013.01); *G16B 20/00* (2019.02); *G16B 25/00* (2019.02); *G16B 30/00* (2019.02)

(58) Field of Classification Search
USPC .......................................................... 702/19
See application file for complete search history.

(56) References Cited

U.S. PATENT DOCUMENTS

2020/0362334 A1* 11/2020 Regev ................. C12N 15/113

OTHER PUBLICATIONS

Fury, Wen, et al. "Overlapping probabilities of top ranking gene lists, hypergeometric distribution, and stringency of gene selection criterion." 2006 international conference of the IEEE engineering in medicine and biology society. IEEE, 2006. (Year: 2006).*
U.S. Appl. No. 62/820,106, filed Mar. 18, 2019, Wen Fury.
PCT, PTC/US2020/023152, Mar. 17, 2020, Regeneron Pharmaceuticals, Inc.
International Search Report and Written Opinion dated Jun. 18, 2020 for application PCT/US2020/023152 filed Mar. 17, 2020 (20 pages).
Swee Hoe Ong et al. "Optimised metrics for CRISPR-KO screens with second generation gRNA libraries" Scientific Reports, vol. 7, No. 1, Aug. 7, 2017, pp. 1-10.
Sanson et al. "Up, down,, and out: optimized libraries for CRISPRa, CRISPRi, and CRIPSR-knockout genetic screens" bioRxiv, Jul. 2018, pp. 1-30.
Michlits et al. "CRISPR-UMI: single-cell lineage tracing of pooled CRISPR-Cas9 screens" Nature Methods, vol. 14, No. 12, Dec. 2017, pp. 1191-1201.
Office Action dated Oct. 31, 2022 for application 3,133,983 filed Sep. 16, 2021 (8 pages).
Ong et al. "Optimised metricsfor CRISPR-KO screens with second-generation gRNA libraries", Scientific Reports, pp. 1-10; Aug. 7, 2017.
Bodapati, S. et al., "A benchmark of algorithms for the analysis of pooled CRISPR screens," Genome Biology, 2020, 13 pgs., vol. 21, issue 62.

* cited by examiner

*Primary Examiner* — G. Steven Vanni
*Assistant Examiner* — Dylan C Jones
(74) *Attorney, Agent, or Firm* — Ballard Spahr

(57) ABSTRACT

Methods and systems for CRISPR positive selection are described. CRISPR positive selection uses DNA sequencing to identify genes that their perturbation by CRISPR guide RNAs is correlated to the phenotype. In some aspects, disclosed are genome-wide CRISPR/Cas9 screening methods to identify genetic modifiers. Also disclosed are the apparatuses used for performing the methods.

23 Claims, 10 Drawing Sheets

110: INFECT A FIRST CULTURE OF CAS9-POSITIVE CELLS WITH A LIBRARY OF VIRAL VECTORS (gRNAs)

↓

120: SEQUENCE THE FIRST CULTURE

↓

130: DETERMINE RESPECTIVE NUMBERS OF gRNAs, PER TARGET REGION AND A TOTAL NUMBER OF gRNAs, OVER ALL TARGET REGIONS, WHOSE READ COUNTS EXCEEDS A BACKGROUND THRESHOLD

↓

140: INFECT A SECOND CULTURE OF CAS9-POSITIVE CELLS WITH A LIBRARY OF VIRAL VECTORS (gRNAs)

↓

150: CATEGORIZE THE CELLS OF THE SECOND CULTURE AS EITHER HAVING A DESIGNATED PHENOTYPE OR NOT HAVING THE DESIGNATED PHENOTYPE

↓

160: SELECT AND SEQUENCE CELLS SELECTED FOR PHENOTYPE

↓

170: DETERMINE RESPECTIVE NUMBERS OF gRNAs, PER TARGET REGION AND A TOTAL NUMBER OF gRNAs, OVER ALL TARGET REGIONS, WHOSE READ COUNTS EXCEEDS A BACKGROUND THRESHOLD

↓

180: DETERMINE, FOR A TARGET REGION OF DNA, A PROBABILITY OF OBSERVING $n'$ gRNAS FOR THE TARGET REGION IN THE SELECTED CELLS BY CHANCE

↓

190: DETERMINE FOR A TARGET REGION OF DNA THAT COMPRISES A GENE, A PROBABILITY OF OBSERVING OR MORE gRNAs OF THE GENE IN THE SELECTED CELLS BY CHANCE

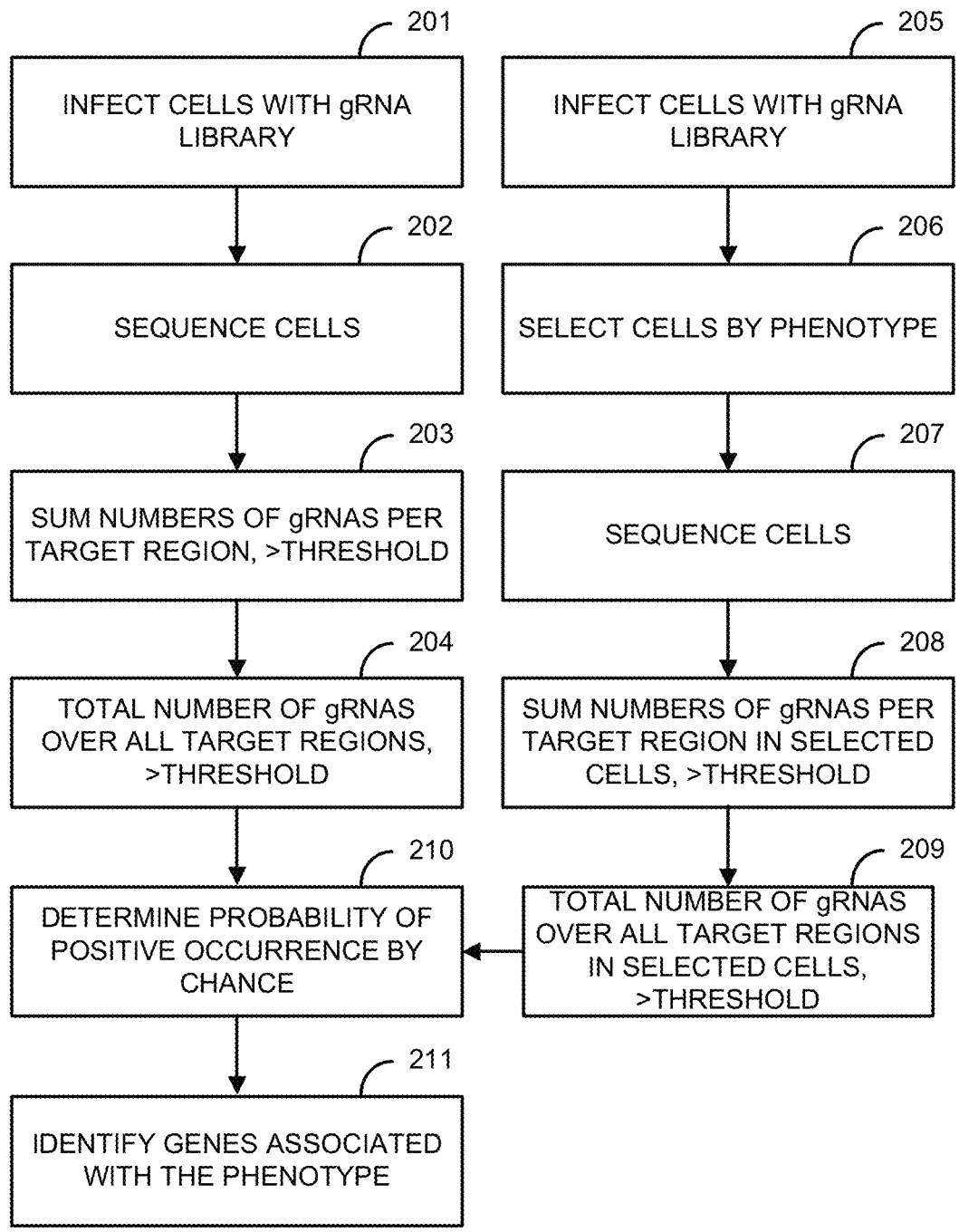

FIG. 4

| Gene # | gRNA per Gene | gRNA Read Count (Pre-selection) | $n$ threshold = 30 | gRNA Read Count (Post-selection) | $n'$ threshold = 30 |
|---|---|---|---|---|---|
| 1 | A<br>B<br>C | A = 100<br>B = 200<br>C = 10 | 2 | A = 0<br>B = 50<br>C = 0 | 1 |
| 2 | D<br>E<br>F | D = 500<br>E = 300<br>F = 200 | 3 | D = 100<br>E = 100<br>F = 100 | 3 |
| 3 | G<br>H<br>I<br>J | G = 200<br>H = 250<br>I = 10<br>J = 300 | 3 | G = 0<br>H = 0<br>I = 0<br>J = 20 | 0 |
| 4 | K<br>L<br>M<br>N | K = 100<br>L = 200<br>M = 200<br>N = 100 | 4 | K = 0<br>L = 0<br>M = 0<br>N = 20 | 0 |
|  |  |  | N=12 |  | N'=4 |

|  | N=63950 | Experiment 1<br>N=4946 | Experiment 2<br>N=13606 |
|---|---|---|---|
|  | $n'$  $n$ | Probability | Probability |
| Target Region 1 | 3 out of 3 | 0.000462378 | 0.009629 |
|  | 2 out of 3 | 0.017017099 | 0.116534 |
|  | 1 out of 3 | 0.214545542 | 0.512117 |
|  | 0 out of 3 | 1 | 1 |
| Target Region 2 | 4 out of 4 | 3.57411E-05 | 0.002048 |
|  | 3 out of 4 | 0.001742291 | 0.032372 |
|  | 2 out of 4 | 0.032291907 | 0.200696 |
|  | 1 out of 4 | 0.275296754 | 0.615924 |
|  | 0 out of 4 | 1 | 1 |

510

| Gene | Guide | Pre-selection | | | | | | | | Post-selection | | | | | |
| | | Exp1 | | Exp2 | | Exp3 | | Exp4 | | Exp1 | | Exp2 | | Exp3 | |
| | | read counts | sum of presence | read counts | sum of presence | read counts | sum of presence | read counts | sum of presence | read counts | sum of presence | read counts | sum of presence | read counts | sum of presence |
|---|---|---|---|---|---|---|---|---|---|---|---|---|---|---|---|
| G1 | g1 | 121 | | 141 | | 335 | | 2012 | | 0 | | 0 | | 5 | |
| | g2 | 1000 | 3 | 342 | 3 | 345 | 3 | 534 | 3 | 8 | 0 | 0 | 0 | 6 | 0 |
| | g3 | 302 | | 300 | | 123 | | 150 | | 12 | | 5 | | 7 | |
| | g4 | 443 | | 598 | | 456 | | 15 | | 4 | | 4 | | 12 | |
| G2 | g5 | 2012 | 4 | 645 | 4 | 789 | 4 | 432 | 3 | 25 | 1 | 3 | 0 | 4 | 0 |
| | g6 | 534 | | 335 | | 141 | | 121 | | 4 | | 18 | | 0 | |
| | g7 | 150 | | 345 | | 342 | | 1000 | | 150 | | 0 | | 6 | |
| G3 | g8 | 150 | 3 | 123 | 3 | 300 | 3 | 302 | 3 | 15 | 2 | 222 | 3 | 1501 | 2 |
| | g9 | 432 | | 456 | | 598 | | 443 | | 432 | | 432 | | 29 | |
| | g10 | 123 | | 789 | | 645 | | 789 | | 123 | | 503 | | 453 | |
| ... | | | | | | | | | | | | | | | |
| G21,000 | g63998 | 231 | 3 | 1050 | 3 | 456 | 3 | 678 | 3 | 0 | 0 | 0 | 1 | 44 | 1 |
| | g63999 | 445 | | 987 | | 899 | | 2009 | | 12 | | 38 | | 0 | |
| | g64000 | 661 | | 123 | | 1021 | | 324 | | 6 | | 0 | | 3 | |
| Sum | 64000 | 20,000,000 | 59,010 | 20,000,000 | 60,123 | 20,000,000 | 60,234 | 20,000,000 | 59,930 | 20,000,000 | 4,320 | 20,000,000 | 8,452 | 20,000,000 | 12,034 |

FIG. 6

Day 3 and 6: without aggregates
Day 10: FRET+

| Gecko A Library | | | |
|---|---|---|---|
| | gRNA | Target | gRNA per Target |
| | 56,116 | 18,874 genes | Mostly 3 |
| | 6,834 | 1,795 microRNA | Mostly 4 |
| | 1000 | None | Unique |
| Total | 63,950 | | |

| Gecko B Library | | | |
|---|---|---|---|
| | gRNA | Target | gRNA per Target |
| | 55,869 | 18,834 genes | Mostly 3 |
| | 0 | microRNA | N/A |
| | 1000 | None | 1 |
| Total | 56,869 | | |

| ID | Experiment | Time | Library |
|---|---|---|---|
| D1036304 | XP5 | Day 3 | Gecko A |
| D1036305 | XP6 | Day 3 | Gecko A |
| D1036306 | XP7 | Day 3 | Gecko A |
| D1036308 | XP8 | Day 3 | Gecko A |
| D1036310 | XP9 | Day 3 | Gecko A |
| D1036307 | XP7 | Day 6 | Gecko A |
| D1036309 | XP8 | Day 6 | Gecko A |
| D1036311 | XP9 | Day 6 | Gecko A |
| D1038281 | XP5 | Day 10 | Gecko A |
| D1038282 | XP6 | Day 10 | Gecko A |
| D1038283 | XP7 | Day 10 | Gecko A |
| D1038284 | XP8 | Day 10 | Gecko A |
| D1038285 | XP9 | Day 10 | Gecko A |
| D1033587 | XP6 | Day 3 | Gecko B |
| D1033589 | XP7 | Day 3 | Gecko B |
| D1033591 | XP8 | Day 3 | Gecko B |
| D1033593 | XP9 | Day 3 | Gecko B |
| D1033586 | XP5 | Day 6 | Gecko B |
| D1033588 | XP6 | Day 6 | Gecko B |
| D1033590 | XP7 | Day 6 | Gecko B |
| D1033592 | XP8 | Day 6 | Gecko B |
| D1033594 | XP9 | Day 6 | Gecko B |
| D1038286 | XP5 | Day 10 | Gecko B |
| D1038287 | XP6 | Day 10 | Gecko B |
| D1038288 | XP7 | Day 10 | Gecko B |
| D1038289 | XP8 | Day 10 | Gecko B |
| D1038290 | XP9 | Day 10 | Gecko B |

FIG. 7

FIG. 9
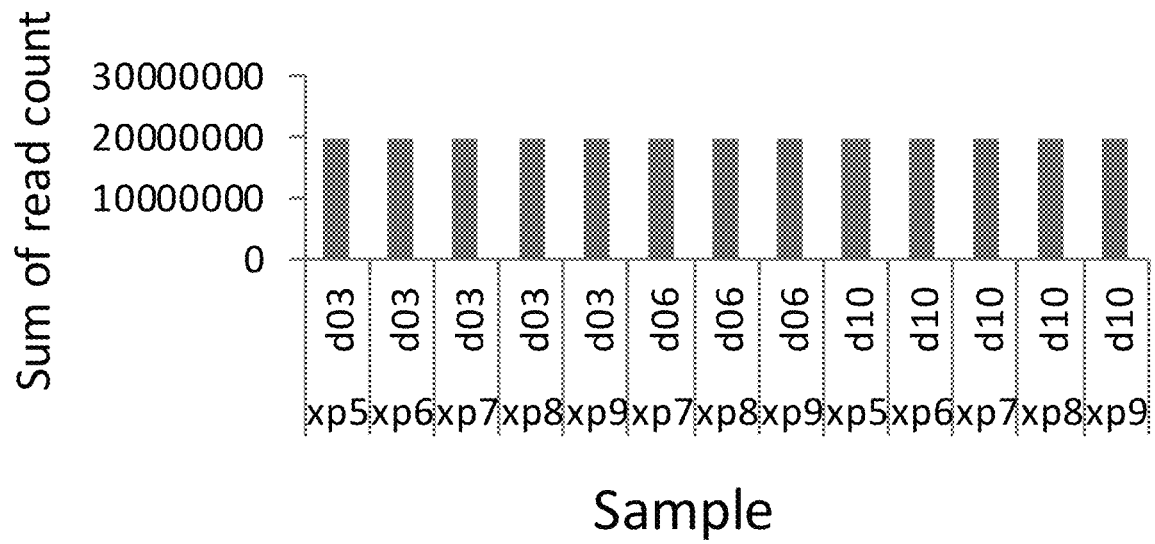
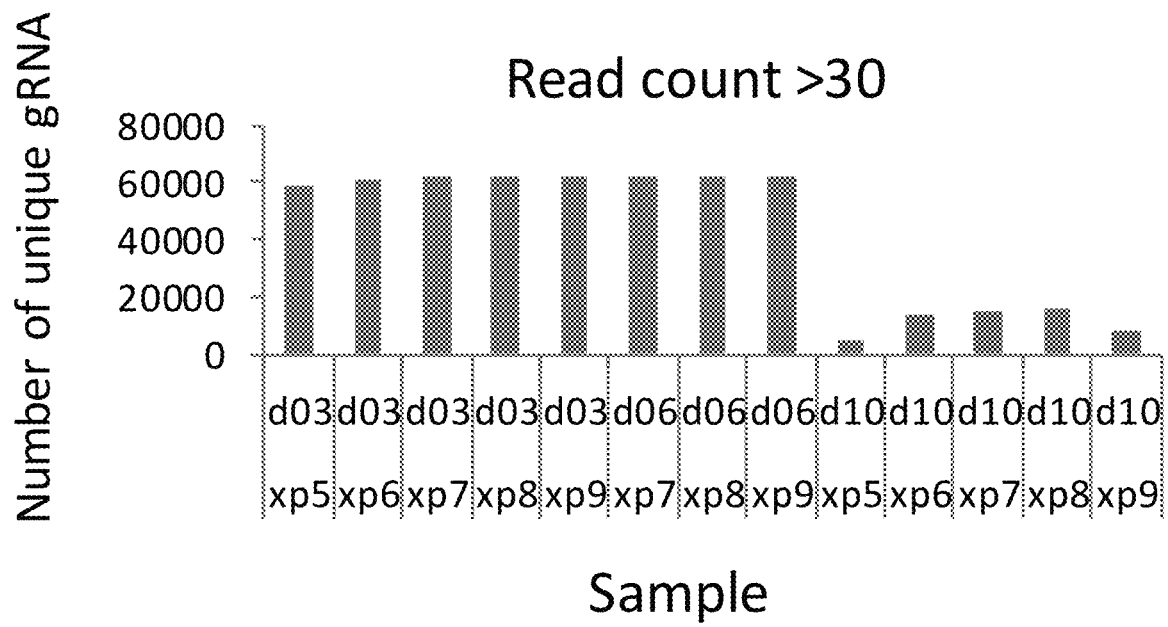

| N=63950 | Experiment 1 N=4946 | Experiment 2 N=13606 | Experiment 3 N=14742 | Experiment 4 N=15468 | Experiment 5 N=7767 |
|---|---|---|---|---|---|
| $n'$ $n$ | Probability | Probability | Probability | Probability | Probability |
| 3 out of 3 | 0.000462378 | 0.009629 | 0.012248 | 0.014149 | 0.001791 |
| 2 out of 3 | 0.017017099 | 0.116534 | 0.134919 | 0.147207 | 0.040666 |
| 1 out of 3 | 0.214545542 | 0.512117 | 0.544405 | 0.564274 | 0.321905 |
| 0 out of 3 | 1 | 1 | 1 | 1 | 1 |
| 4 out of 4 | 3.57411E-05 | 0.002048 | 0.002823 | 0.003422 | 0.000217 |
| 3 out of 4 | 0.001742291 | 0.032372 | 0.040524 | 0.04633 | 0.006512 |
| 2 out of 4 | 0.032291907 | 0.200696 | 0.229313 | 0.248084 | 0.074821 |
| 1 out of 4 | 0.275296754 | 0.615924 | 0.649435 | 0.669671 | 0.404267 |
| 0 out of 4 | 1 | 1 | 1 | 1 | 1 |

FIG. 10

METHODS AND SYSTEMS FOR CRISPR SELECTION

CROSS REFERENCE TO RELATED PATENT APPLICATION

This application claims priority to U.S. Provisional Application No. 62/820,106, filed Mar 18, 2019, herein incorporated by reference in its entirety.

BACKGROUND

Clustered regularly interspaced short palindromic repeats (CRISPR)-Cas9 technology has revolutionized genome engineering. In this system, guide RNAs (gRNAs) direct Cas9 nucleases to induce double-strand breaks at targeted genomic regions. The 5' end of gRNAs includes a nucleotide sequence of around 20 nucleotides that is complementary to the targeted region. When the double-strand breaks are repaired by non-homologous end-joining (NHEJ), insertions and deletions occur with high frequency, thus efficiently knocking out the targeted genomic loci. The development of a lentiviral delivery method has enabled the creation of genome-scale CRISPR/Cas9 knockout libraries. These libraries allow both negative and positive selection screening to be conducted on mammalian cell lines. In CRISPR/Cas9 knockout screens, each gene is targeted by several gRNAs, and the mutant pool carrying different gene knockouts could be determined by high-throughput sequencing. CRISPR activation (CRISPRa) can also be used with gRNA libraries wherein the activated genes could be determined by high-throughput sequencing.

The genome-wide CRISPR/Cas9 knockout or gene activation technology is an effective gene perturbation screen technique. The goal is to identify the gRNAs, therefore corresponding affected genes, associated with a phenotype. However, the data generated by these screens pose several challenges to computational analysis. CRISPR studies are often carried out with multiple replicates. CRISPR is susceptible to variability in that each experiment may not use the same gRNA virus titers in the screening library, lentivirus infection rates may vary among experiments, and the gRNAs may not target genes with the same efficiency among the experiments. Therefore the observed gRNA abundance is highly variable across experiments even with the cells of the same phenotype. Existing techniques rely on read counts to identify gRNAs associated with a phenotype, specifically using mean and variance of normalized gRNA read counts to test whether gRNA abundance differs significantly between cells with or without a phenotype.

However, such techniques do not address the inter-experiment variability issues stated above and rather assume a high degree of homogeneity between pre-selection and post-selection experiments. These techniques do not address variability within a single CRISPR experiment and/or between CRISPR experiments.

Thus, there is a need for technical improvements in computing technology that addresses CRISPR variability issues when identifying genes through positive and negative selection screens.

BRIEF SUMMARY

It is to be understood that both the following general description and the following detailed description are exemplary and explanatory only and are not restrictive.

In one embodiment, a method comprises (A) infecting a first culture of cas9-positive cells with a library of viral vectors, the library comprising at least 3 guide RNAs (gRNAs) for cleaving a target region of DNA within the genome of the cells; sequencing the cells to obtain a read count for each of the gRNAs; summing ($\Sigma$) respective numbers of gRNAs, per target region of DNA, whose read count exceeds a background threshold, wherein $\Sigma=n$; and summing ($\Sigma$) a total number of gRNAs, over all target regions, whose read count exceeds the background threshold, wherein $\Sigma=N$. The method comprises (B) infecting a second culture of cas9-positive cells with the library of viral vectors; categorizing the cells of the second culture as either having a designated phenotype or not having the designated phenotype; selecting cells having the designated phenotype and sequencing the selected cells to obtain a post-selection read count for each of the gRNAs; summing ($\Sigma$) respective numbers of gRNAs, per target region of DNA, in the selected cells whose post-selection read count exceeds the background threshold, wherein $\Sigma=n'$; and summing ($\Sigma$) a total number of gRNAs, over all target regions, of the selected cells whose read count exceeds the threshold, wherein $\Sigma=N'$. The method comprises (C) calculating, for a target region of DNA, a probability of observing n' gRNAs for the target region in the selected cells by chance according to the formula $$\frac{\binom{n'}{n}\cdot\binom{N'-n'}{N-n}}{\binom{N'}{N}}, \text{ wherein } \binom{x}{y} = \frac{y!}{x!(y-x)!}$$

computes a number of ways of choosing x objects out of y objects; and calculating, for a target region of DNA that comprises a gene, a probability of observing n' or more gRNAs of the gene in the selected cells by chance according to the formula $$\sum_{i=n'}^{n} \frac{\binom{i}{n}\cdot\binom{N'-i}{N-n}}{\binom{N'}{N}}.$$

In one embodiment, a method comprises determining, based on sequencing a first cell population after infection with a vector comprising a library of at least 3 guide RNAs (gRNAs) for each of a plurality of target regions of DNA, a respective number of gRNAs (n) present for each of the plurality of target regions of DNA, whose read count exceeds a background threshold, determining, based on the respective numbers of gRNAs for each of the plurality of target regions of DNA, a total number of gRNAs (N) present in the first cell population, over all target regions of the plurality of target regions of DNA, whose read count exceeds the background threshold, determining, based on sequencing a second cell population after infection with a vector comprising the library of at least 3 gRNAs for each of the plurality of target regions of DNA, a respective number of gRNAs (n') present for each of the plurality of target regions of DNA, whose read count exceeds the background threshold, determining, based on the respective numbers of gRNAs for each of the plurality of target regions of DNA, a total number of gRNAs (N') present in the second cell population over all target regions of the plurality of target regions of DNA whose read count exceeds the background threshold, determining, for each target region of the plurality of target regions, based on n, N, n', and N', a probability of observing n' gRNAs for the target region in the selected cells by chance, determining, for a target region that comprises a sequence of interest, based on the probability of observing n' gRNAs for the target region in the selected cells by chance, a probability of observing n' or more gRNAs of the sequence of interest in the selected cells by chance, and identifying, based on the probability of observing n' or more gRNAs of the sequence of interest in the selected cells by chance, that the sequence of interest is positively selected.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 1 is an example method for CRISPR positive selection;

FIG. 2 shows another example method;

FIG. 4 shows an example data structure storing artificial read counts for four hypothetical genes, with either three (A-C or D-F) or four (G-J or K-N) gRNA per gene, whereby a pre-selection and post-selection read count of each gRNA is taken, and whereby the pre-selection n and post-selection n' read counts above a threshold of 30 are identified and added together (N and N'), and the probability is determined according to the formulae shown;

FIG. 5 shows an example data structure storing artificial data and artificial results of the disclosed methods whereby N number of gRNA were used initially, with N' number of gRNA present after 10 days in cell culture. As shown, Target Region 1 or Target Region 2 has n number of gRNA and the chance for n' number of gRNA present in the cells after 10 days of culture is presented (Probability presented as a p value);

FIG. 6 shows the results of an experiment involving approximately 21,000 genes (G #), with the read counts of each gRNA (g) from four pre-selection and three post-selection experiments shown and the number of read counts added together (Sum) and read counts above a threshold of 30 identified (sum of presence) and added together (Sum);

FIG. 7 shows a sample gRNA library (Gecko A and Geck B) used in a number of parallel experiments (xp #) over three (d03), six (d06) and ten (d10) days of cell culture, after which Tau aggregation as measured by FRET fluorescence was determined; the constitution of the Gecko A and B libraries is shown as including specific gene-targeting gRNA, specific microRNA-targeting gRNA, and non-targeting gRNA and the approximate number of gRNA per target;

FIG. 9 shows normalization of the read counts of the Gecko A library from the experiments shown in FIG. 8, normalization is based on the median of the read counts and day 10 is post-selection; and FIG. 10 shows that since a target may have different number of gRNA and also some samples have many more "present" gRNA than others at day 10, an alternative way to tally the frequency of "presence" is to calculate the probability of a gene being "present." The probability was calculated for five different genes screened on day 10 (post-selection) using Gecko A library gRNA.

DETAILED DESCRIPTION

Figure 3:
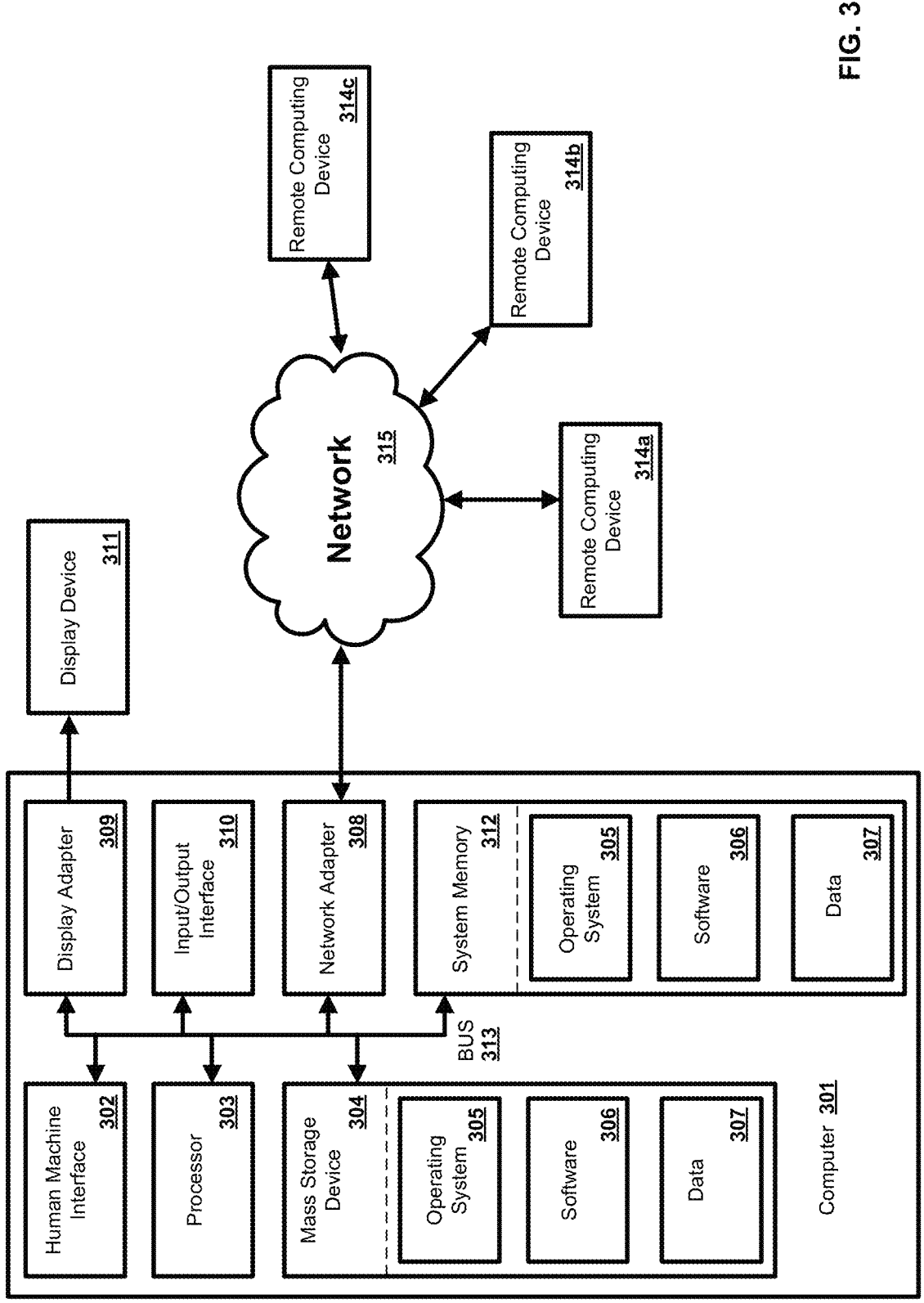
FIG. 3 shows an example operating environment.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise.

As used herein, the term "probe" and "guide RNA (gRNA)" "and "guide" are used interchangeably. In one embodiment, the gRNA can also be provided in the form of DNA encoding the gRNA.

As used herein, "Cas proteins" can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins.

In a first aspect, the disclosure features methods for identifying genes or gene products, e.g., that modulate the expression of other genes or gene products. The methods are useful, for example, to demonstrate positive selection following perturbation with CRISPR guides.

In one embodiment (shown in FIG. 1), the method comprises the steps of infecting a first culture of cas9-positive cells with a library of viral vectors 110, the library comprising at least 3 guide RNAs for cleaving a target region of DNA within the genome of the cells, sequencing the cells to obtain a read count for each of the gRNAs 120, summing ($\Sigma$) respective numbers of gRNAs, per target region of DNA, whose read count exceeds a background threshold ($\Sigma$=n) and summing ($\Sigma$) a total number of gRNAs, over all target regions, whose read count exceeds the background threshold ($\Sigma$=N) 130, infecting a second culture of cas9-positive cells with the library of viral vectors 140, categorizing the cells of the second culture as either having a designated phenotype or not having the designated phenotype 150, selecting cells having the designated phenotype and sequencing the selected cells to obtain a post-selection read count for each of the gRNAs 160, summing ($\Sigma$) respective numbers of gRNAs, per target region of DNA, in the selected cells whose post-selection read count exceeds the background threshold ($\Sigma$=n'), and summing ($\Sigma$) a total number of gRNAs, over all target regions, of the selected cells whose read count exceeds the threshold ($\Sigma$=N') 170, calculating, for a target region of DNA, a probability of observing n' gRNAs for the target region in the selected cells by chance according to the formula $$\frac{\binom{n'}{n}\cdot\binom{N'-n'}{N-n}}{\binom{N'}{N}} 180, \text{ wherein } \binom{x}{y} = \frac{y!}{x!(y-x)!}$$

computes a number of ways of choosing x objects out of y objects, and calculating, for a target region of DNA that comprises a gene, a probability of observing n' or more gRNAs of the gene in the selected cells by chance according to the formula $$\sum_{i=n'}^{n} \frac{\binom{i}{n}\cdot\binom{N'-i}{N-n}}{\binom{N'}{N}} 190.$$

In one embodiment (also shown in FIG. 1), the method comprises the steps of infecting a first culture of cas9-positive cells with a library of viral vectors 110, the library comprising at least 3 guide RNAs (gRNAs) for enhancing transcription of a target region of DNA within the genome of the cells, sequencing the cells to obtain a read count for each of the gRNAs 120, summing (Σ) respective numbers of gRNAs, per target region of DNA, whose read count exceeds a background threshold (Σ=n) and summing (Σ) a total number of gRNAs, over all target regions, whose read count exceeds the background threshold (Σ=N) 130, infecting a second culture of cas9-positive cells with the library of viral vectors 140, categorizing the cells of the second culture as either having a designated phenotype or not having the designated phenotype 150, selecting cells having the designated phenotype and sequencing the selected cells to obtain a post-selection read count for each of the gRNAs 160, summing (Σ) respective numbers of gRNAs, per target region of DNA, in the selected cells whose post-selection read count exceeds the background threshold (Σ=n'), and summing (Σ) a total number of gRNAs, over all target regions, of the selected cells whose read count exceeds the threshold (Σ=N') 170, calculating, for a target region of DNA, a probability of observing n' gRNAs for the target region in the selected cells by chance according to the formula $$\frac{\binom{n'}{n}\cdot\binom{N'-n'}{N-n}}{\binom{N'}{N}} 180, \text{ wherein } \binom{x}{y} = \frac{y!}{x!(y-x)!}$$

computes a number of ways of choosing x objects out of y objects, and calculating, for a target region of DNA that comprises a gene, a probability of observing n' or more gRNAs of the gene in the selected cells by chance according to the formula $$\sum_{i=n'}^{n} \frac{\binom{i}{n}\cdot\binom{N'-i}{N-n}}{\binom{N'}{N}} 190.$$

In one embodiment, the first culture can be infected according to a CRISPR technique. In one embodiment, infecting a first culture of cas9-positive cells with a library of viral vectors (e.g. FIG. 2; 201) and infecting a second culture of cas9-positive cells with the library of viral vectors (e.g. FIG. 2; 205) comprises using a CRISPR gRNA library. A CRISPR gRNA library can be a knockout library, including, for example, genome-wide gRNA knockout libraries that include one or more gRNAs (e.g., sgRNAs) targeting each gene in a genome, wherein the genome can be any type of genome. In some embodiments, a gRNA library may comprise a pooled library. A non-limiting example of a pooled library includes the genome-scale CRISPR knock out (GeCKO) library. See, e.g., Shalem O et al. (2014) Science 343:84-7 and Sanjana N E et al. (2014) Nat. Methods 11:783-4. The gRNAs in a library can target any number of target regions (e.g. genes) in a DNA. For example, the gRNAs can target about 50 or more genes, about 100 or more genes, about 200 or more genes, about 300 or more genes, about 400 or more genes, about 500 or more genes, about 1000 or more genes, about 2000 or more genes, about 3000 or more genes, about 4000 or more genes, about 5000 or more genes, about 10000 or more genes, or about 20000 or more genes. In some libraries, the gRNAs can be selected to target genes in a particular signaling pathway. The gRNA libraries can be administered using a wide range of multiplicities of infection (MOIs). In some aspects, a lower MOI can be used to encourage infection resulting in one gRNA per cell.

In one embodiment, the cas-positive cells can comprise a cas protein for cleaving a target region of DNA or a cas protein for regulating transcription (e.g. enhancing or repressing transcription). A cas protein for cleaving a target region of DNA can comprise an RNA binding domain and a nuclease domain. A cas protein for regulating transcription is deactivated so that it no longer has nuclease activity. Deactivated Cas (e.g. dCas-9) can be fused to a transcription activator or transcription repressor. Thus, disclosed in one embodiment are cas-9 positive cells comprising cas-9 with wild type activity or deactivated cas-9. The deactivated cas-9 can be, for example, fused to at least one transcription activation domain. The one or more gRNAs can bind to a target sequence upstream of a transcription start site of a gene of interest and instead of cleaving the DNA, the dCas-9 and the transcription modulators can play a role in either activating transcription or repressing transcription of the gene of interest. If the dCas-9 is fused to one or more transcription activators then the one or more transcription activators will recruit transcription factors to the transcription start site of the gene of interest thus activating or up-regulating transcription. If the dCas-9 is fused to a transcription repressor, then transcription will be inhibited, down-regulated, or repressed.

In one embodiment, a target region of DNA can be a gene. In one embodiment, a target region of DNA can be a promoter region or a regulatory element region of a gene. In one embodiment, the target region of DNA regulates a downstream gene or protein. In one embodiment, regulating a downstream gene or protein comprises the activation or inhibition of the downstream gene or protein.

In some embodiments, the cells comprise a selectable marker system. For example, as disclosed in the methods herein the cas-9 positive cells of the first culture can be modified to contain one or more selectable markers. A selectable marker system can involve a marker protein or proteins fused or linked to a selectable marker that is only activated upon the protein or proteins being regulated. A "marker protein or proteins" can be any protein that can be regulated, wherein being regulated means the marker protein changes shape, binds to one or more other proteins or nucleic acids, has a change in activity, or has a change in expression level. The marker protein or proteins can be regulated by a gene being targeted by one or more gRNAs so that if the gene is cleaved by the Cas9 then the marker protein or proteins are not regulated resulting in the selectable marker not being activated. Thus, one can select the cells without the activated selectable marker as those cells comprising a gene that regulates the marker protein or proteins fused or linked to the selectable marker in the cells. For example, Tau can be fused or linked to CFP. Another Tau protein can be fused or linked to YFP. Upon aggregation of the tau proteins, light that hits the CFP is then emitted as a blue light that excites YFP which in turn emits a yellow light. If there is no aggregation of the tau proteins, the blue light emitted from the CFP cannot excite the YFP of the other tau protein and therefore no yellow light is emitted. Thus, if a gene that regulates tau is targeted by one or more gRNAs and is therefore cleaved, no yellow light will be emitted. In the end, this gene can be identified as a gene that regulates Tau (e.g. causes Tau aggregation). In CRISPRa, if a gRNA binds to a target region, activation of the downstream gene results and therefore cells with an overexpression or excess amount of the selectable marker can be selected. For example, using the Tau proteins as described above, an increased amount of yellow light compared to cells without gRNA can indicate a gene that regulates Tau. Any number of proteins present in a known pathway, specifically a disease pathway, can be used as marker proteins in order to identify genes that regulate that marker protein and ultimately can be found to be involved in a particular disease.

In one embodiment, the set of cells may be categorized and selected (e.g., by phenotype) (e.g., FIG. 2; 206) can be performed some amount of time after initial infection, for example, 1, 2, 3, 4, 5, 6, 7, 8, 9, 10, 11, 12, 13, 14, 15 days, and the like, after infection. In an embodiment, many types of screens/selection mechanisms may be used that takes advantage of the selectable markers contained in the set of cells. In one embodiment, the selection mechanism comprises one or more of exposing the second cell population to a drug or exposing the second cell population to a substance that identifies protein activity or expression levels. In one embodiment, selecting cells having the designated phenotype comprises sorting the cells based on the one or more selectable markers. In one embodiment, the viability of a cell can be used for selection.

In one embodiment, categorizing the cells of the second culture as either having a designated phenotype or not having the designated phenotype comprises identifying the presence or absence of the designated phenotype in the cells. Categorizing cells of the second culture as either having the designated phenotype or not having the designated phenotype can comprise applying a selection mechanism to the second cell culture. In one embodiment, once the phenotype has been identified, selecting cells having the designated phenotype (or not having the designated phenotype) can be performed. A phenotype is any observable characteristic or functional effect that can be measured in an assay such as changes in cell growth, proliferation, morphology, enzyme function, signal transduction, expression patterns, downstream expression patterns, reporter gene activation, hormone release, growth factor release, neurotransmitter release, ligand binding, apoptosis, and product formation. In one embodiment, the designated phenotype can be fluorescence or cell survival.

The cells can be modified to convey a phenotype that can be directly selected for, for example, by genomic integration of a marker or by the presence of an intracellular marker that is not integrated in the genome. As used herein, "marker" most generally refers to a biological feature or trait that, when present in a cell (e.g., is expressed), results in an attribute or phenotype that visualizes or identifies the cell as containing that marker. A variety of marker types are commonly used, and can be, for example, visual markers such as color development, e.g., lacZ complementation (β-galactosidase) or fluorescence, e.g., such as expression of green fluorescent protein (GFP) or GFP fusion proteins, RFP, BFP, luciferase, β-galactosidase, enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase, phenotypic markers (growth rate, cell morphology, colony color or colony morphology, temperature sensitivity), auxotrophic markers (growth requirements), antibiotic sensitivities and resistances, molecular markers such as biomolecules that are distinguishable by antigenic sensitivity (e.g., blood group antigens and histocompatibility markers), cell surface markers (for example H2KK), enzymatic markers, and nucleic acid markers, for example, restriction fragment length polymorphisms (RFLP), single nucleotide polymorphism (SNP) and various other amplifiable genetic polymorphisms. Thus, for example, the one or more selectable markers can be a detectable enzyme such as β-galactosidase or luciferase A "selectable marker" or "screening marker" or "positive selection marker" refers to a marker that, when present in a cell, results in an attribute or phenotype that allows selection or segregation of those cells from other cells that do not express the selectable marker trait. A variety of genes may be used as selectable markers, e.g., genes encoding drug resistance or auxotrophic rescue are widely known. For example, kanamycin (neomycin) resistance can be used as a trait to select bacteria that have taken up a plasmid carrying a gene encoding for bacterial kanamycin resistance (e.g., the enzyme neomycin phosphotransferase II). Non-transfected cells will eventually die off when the culture is treated with neomycin or similar antibiotic. The set of cells may be used in drug screens to identify genes that confer drug-resistance. Cells may be treated with a drug of interest and gRNAs that are enriched are associated with genes that confer drug resistance when mutated. Screens for resistance to viral or bacterial pathogens may be used to identify genes that prevent infection or pathogen replication. As in drug resistance screens, survival after pathogen exposure provides strong selection. In cancer, negative selection CRISPR screens may identify "oncogene addictions" in specific cancer subtypes that can provide the foundation for molecular targeted therapies. For developmental studies, screening in human and mouse pluripotent cells may pinpoint genes required for pluripotency or for differentiation into distinct cell types.

In one embodiment, the cells comprise a selectable marker system. A selectable marker system can involve a fluorescent protein FRET biosensor. For example, Tau can be fused or linked to CFP. Another Tau protein can be fused or linked to YFP. Upon aggregation of the tau proteins, light that hits the CFP is then emitted as a blue light that excites YFP which in turn emits a yellow light. If there is no aggregation of the tau proteins, the blue light emitted from the CFP cannot excite the YFP of the other tau protein and therefore no yellow light is emitted. Thus, if a gene that regulates tau is targeted by one or more gRNAs and is therefore cleaved, no yellow light will be emitted. In the end, this gene can be identified as a gene that regulates Tau (e.g. causes Tau aggregation). In CRISPRa, if a gRNA binds to a target region, activation of the downstream gene results and therefore cells with an overexpression or excess amount of the selectable marker can be selected. For example, using the Tau protein FRET biosensor as described above, an increased amount of yellow light compared to cells without gRNA can indicate the gRNA bound to a gene that regulates Tau. Any number of proteins present in a known pathway, specifically a disease pathway, can be used as marker proteins in order to identify genes that regulate that marker protein and ultimately can be found to be involved in a particular disease pathway.

In one embodiment, the cells of the first culture and the selected cells of the second culture may be sequenced (e.g. FIG. 2; 202 and 207). The cells of the first culture and the selected cells of the second culture may be sequenced at different times after infection. The cells of the first culture and the selected cells of the second culture may be sequenced at different times after infection in order to generate read counts before selection (cells of the first culture) and to generate read counts after selection (selected cells of the second culture). For example, the cells of the first culture may be sequenced 3 days after infection and the selected cells of the second culture may be sequenced 10 days after infection. The cells can be sequenced using any available sequencing technique, such as NGS. The nucleic acids of the cells can be sequenced to generate sequence data. The sequence data can comprise read counts. The sequence data can comprise read counts for one or more gRNAs of the library. Sequencing the cells can generate sequence data that can be stored in a data structure. The data structure can comprise one or more nucleic acid sequences and/or a sample identifier.

The read counts resulting from the sequencing suffer the traditional biases that exist in CRISPR screen analyses, including frequent absence of replicates, variability in gRNA knockout efficiencies, and variability in read count distributions. These biases result in poor results when analyzing read counts according to negative binomial approaches, $\log_2$-ratio approaches, and paired t-test approaches. Such approaches require a certain degree of homogeneity/agreement among the gRNAs for the same gene as well as among repeats. These existing approaches cannot handle large variation among gRNAs and repeats for the same gene that can result from, for example, different infection efficiency, different gene editing efficiency, initial viral counts in the screening library, and the presence of other guides with the same phenotype. These biases can exist within a CRISPR experiment and between multiple CRISPR experiments. The presently described steps determining the sum numbers of gRNAs per target region and the total number of gRNAs over all the target regions represent read count processing that is robust to large variations in the read counts. As one embodiment of the disclosed methods is based on the positive occurrences of guides per gene in an individual experiment, instead of the exact read count of each guide, it provides an advantage over the existing approaches.

The read counts can be normalized. For example, read counts from different samples can be median-normalized to adjust for the effect of library sizes and read count distributions. In an embodiment, given N CRISPR/Cas9 knockout screening experiments performed on a set of M gRNAs, and the read count of gRNA i in experiment j is $x_{ij}$, $1 \leq i \leq M$, $1 \leq j \leq N$. Since the sequencing depths (or library sizes) may differ between experiments, the read counts can be adjusted by applying a median ratio method to all experiments. In an embodiment, the adjusted read count $x'_{ij}$ may be calculated according to the equation:

$$x'_{ij} = \frac{x_{ij}}{\sum_{i=1}^{N} x_{ij}} * S$$

wherein S is the median of $(\Sigma_{i=1}^{N} x_{i1}, \Sigma_{i=1}^{N} x_{i2}, \ldots \Sigma_{i=1}^{N} x_{iM})$ for j=1 to M. In another embodiment, the adjusted read count $x'_{ij}$ may be calculated as the rounded value of $x_{ij}/s_j$, where $s_j$ is the size factor in experiment j and computed as the median of all size factors calculated from individual sgRNA read counts:

$$s_j = median_i \left\{ \frac{x_{ij}}{\hat{x}_i} \right\}$$

where x̂i is the geometric mean of the read counts of gRNA i: $\hat{x}_i = (\Pi_{k=1}^{N} x_{ik})^{1/N}$.

Alternatively, read counts per gRNA and per gene may be normalized using either counts per million, total, or size-factor normalization. See, Anders, S. and Huber, W. (2010) Differential expression analysis for sequence count data. *Genome Biol.*, 11, R106, incorporated herein by reference in its entirety.

In one embodiment, the disclosed methods use the sequence data to determine a sum ($\Sigma$) of respective numbers of gRNAs (n'), per target region of DNA, in the selected cells whose post-selection read count exceeds the background threshold (e.g. FIG. 2; 203, 208). The methods can also include determining a total number of gRNAs (N'), over all target regions, of the selected cells whose read count exceeds the background threshold (e.g. FIG. 2; 204, 209).

The disclosed methods can thus identify positive occurrences of gRNAs from the library in the sequences of the selected cells. The sequence data comprising read counts can be analyzed to determine, for each target region of DNA (e.g., a gene), a post-selection "sum of presence," or n'. The "sum of presence," or the respective numbers of gRNAs present per target region of DNA, may be determined by comparing the individual read counts of each gRNA to a background threshold. Determining the respective numbers of gRNAs, per target region of DNA, whose read count exceeds a background threshold can be performed by a computing device. The background threshold can be any value sufficient to reduce background noise in the sequence data. For example, 30 may be used as the background threshold. Accordingly, the "sum of presence" indicates the number of gRNAs present (whose read counts exceed the background threshold), in contrast with the quantity of gRNAs present which is indicated by the read counts.

In one embodiment, the steps of infecting a second culture of cas9-positive cells with the library of viral vectors; categorizing the cells of the second culture as either having a designated phenotype or not having the designated phenotype; selecting cells having the designated phenotype and sequencing the selected cells to obtain a post-selection read count for each of the gRNAs; summing ($\Sigma$) respective numbers of gRNAs, per target region of DNA, in the selected cells whose post-selection read count exceeds the background threshold, wherein $\Sigma=n'$; and summing ($\Sigma$) a total number of gRNAs, over all target regions, of the selected cells whose read count exceeds the threshold, wherein $\Sigma=N'$ can be repeated any number of times.

In one embodiment, the disclosed methods further comprise identifying, based on the probability of observing n' or more gRNAs of the gene in the selected cells by chance, that the target region is positively selected (e.g. FIG. 2; 211). In some embodiments, identifying that the target region is positively selected comprises determining that the probability of observing n' or more gRNAs of the sequence of interest in the selected cells by chance satisfies a threshold.

In some embodiments, the disclosed methods further comprise identifying, based on the probability of observing n' or more gRNAs of the gene in the selected cells by chance, the target region as a modifier of a second gene. In some embodiments, the disclosed methods further comprise identifying, based on the probability of observing n' or more gRNAs of the gene in the selected cells by chance, the target region as a therapeutic target. In some embodiments, the disclosed methods further comprise identifying, based on the probability of observing n' or more gRNAs of the gene in the selected cells by chance, the target region as correlated with the designated phenotype. In some embodiments, the disclosed methods further comprise identifying, based on the probability of observing n' or more gRNAs of the gene in the selected cells by chance, the target region as exhibiting a protective effect. Thus, the disclosed methods can help identify target regions (e.g., genes) involved in a disease pathway, involved in regulation of one or more other genes/proteins, and/or otherwise associated with the phenotype. A region of DNA (e.g., a candidate gene) may be "associated with" a selected phenotype if modulation of gene expression of the candidate gene causes a change in the selected phenotype In one embodiment, the disclosed methods further comprise determining, for each gRNA, an enrichment score. In some embodiments, determining, for each gRNA, the enrichment score comprises evaluating N/N'. The enrichment score may be determined to exceed a threshold. The threshold may be relative to other enrichment scores for other target regions. A target region with a high enrichment score and a low probability that gRNAs are present by chance may be used to identify the target region as being associated with the phenotype.

In an exemplary embodiment, the methods and systems can be implemented on a computer 301 as illustrated in FIG. 3 and described below. Similarly, the methods and systems can utilize one or more computers to perform one or more functions in one or more locations. FIG. 3 is a block diagram illustrating an exemplary operating environment for performing the methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices.

The processing of the methods and systems can be performed by software components. The systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The methods can also be practiced in grid-based and distributed computing environments where tasks are performed by remote processing devices that are linked through a communications network. In a distributed computing environment, program modules can be located in both local and remote computer storage media including memory storage devices.

Further, the systems and methods can be implemented via a computing device in the form of a computer 301. The components of the computer 301 can comprise, but are not limited to, one or more processors 303, a system memory 312, and a system bus 313 that couples various system components including the one or more processors 303 to the system memory 312. The system can utilize parallel computing.

The system bus 313 represents one or more of several possible types of bus structures, including a memory bus or memory controller, a peripheral bus, an accelerated graphics port, or local bus using any of a variety of bus architectures. The bus 313, and all buses specified in this description can also be implemented over a wired or wireless network connection and each of the subsystems, including the one or more processors 303, a mass storage device 304, an operating system 305, software 306, data 307, a network adapter 308, the system memory 312, an Input/Output Interface 310, a display adapter 309, a display device 311, and a human machine interface 302, can be contained within one or more remote computing devices 314a,b,c at physically separate locations, connected through buses of this form, in effect implementing a fully distributed system.

The computer 301 typically comprises a variety of computer readable media. Exemplary readable media can be any available media that is accessible by the computer 301 and comprises, for example and not meant to be limiting, both volatile and non-volatile media, removable and non-removable media. The system memory 312 comprises computer readable media in the form of volatile memory, such as random access memory (RAM), and/or non-volatile memory, such as read only memory (ROM). The system memory 312 typically contains data such as the data 307 and/or program modules such as the operating system 305 and the software 306 that are immediately accessible to and/or are presently operated on by the one or more processors 303.

In another embodiment, the computer 301 can also comprise other removable/non-removable, volatile/non-volatile computer storage media. By way of example, FIG. 3 illustrates the mass storage device 304 which can provide non-volatile storage of computer code, computer readable instructions, data structures, program modules, and other data for the computer 301. For example and not meant to be limiting, the mass storage device 304 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), and/or electrically erasable programmable read-only memory (EEPROM).

Optionally, any number of program modules can be stored on the mass storage device 304, including by way of example, the operating system 305 and the software 306. Each of the operating system 305 and the software 306 (or some combination thereof) can comprise elements of the programming and the software 306. The data 307 can also be stored on the mass storage device 304. The data 307 can be stored in any of one or more databases. Examples of such databases comprise, DB2®, MICROSOFT® Access, MICROSOFT® SQL Server, ORACLE®, and/or MYSQL®, POSTGRESQL®. The databases can be centralized or distributed across multiple systems. The data 307 may comprise sequencing data. The sequencing data may comprise sequencing read data (e.g., read counts). The computer 301 may receive first read count data generated, for example, at steps 120 and 202 of FIG. 1 and FIG. 2, respectively. The computer 301 may receive second read count data generated, for example, at steps 160 and 207 of FIG. 1 and FIG. 2, respectively.

In another embodiment, the user can enter commands and information into the computer 301 via an input device (not shown). Examples of such input devices comprise, but are not limited to, a keyboard, pointing device (e.g., a "mouse"), a microphone, a joystick, a scanner, tactile input devices such as gloves, and/or other body coverings. These and other input devices can be connected to the one or more processors 303 via the human machine interface 302 that is coupled to the system bus 313, but can be connected by other interface and bus structures, such as a parallel port, game port, an IEEE 1394 Port (also referred to as a Firewire port), a serial port, or a universal serial bus (USB).

In yet another embodiment, the display device 311 can also be connected to the system bus 313 via an interface, such as the display adapter 309. It is contemplated that the computer 301 can have more than one display adapter 309 and the computer 301 can have more than one display device 311. For example, a display device can be a monitor, an LCD (Liquid Crystal Display), or a projector. In addition to the display device 311, other output peripheral devices can comprise components such as speakers (not shown) and a printer (not shown) which can be connected to the computer 301 via the Input/Output Interface 310. Any step and/or result of the methods can be output in any form to an output device. Such output can be any form of visual representation, including, but not limited to, textual, graphical, animation, audio, and/or tactile. The display 311 and computer 301 can be part of one device, or separate devices.

The computer 301 can operate in a networked environment using logical connections to one or more remote computing devices 314a,b,c. By way of example, a remote computing device can be a personal computer, portable computer, smartphone, a server, a router, a network computer, a peer device or other common network node, and so on. Logical connections between the computer 301 and a remote computing device 314a,b,c can be made via a network 315, such as a local area network (LAN) and/or a general wide area network (WAN). Such network connections can be through the network adapter 308. The network adapter 308 can be implemented in both wired and wireless environments. In an embodiment, the system memory 312 can store one or more objects made accessible to the one or more remote computing devices 314a,b,c via the network 315. Thus, the computer 301 can serve as cloud-based object storage. In another embodiment, one or more of the one or more remote computing devices 314a,b,c can store one or more objects made accessible to the computer 301 and/or the other of the one or more remote computing devices 314a,b,c. Thus, the one or more remote computing devices 314a,b,c can also serve as cloud-based object storage.

For purposes of illustration, application programs and other executable program components such as the operating system 305 are illustrated herein as discrete blocks, although it is recognized that such programs and components reside at various times in different storage components of the computing device 301, and are executed by the one or more processors 303 of the computer. In an embodiment, at least a portion of the software 306 and/or the data 307 can be stored on and/or executed on one or more of the computing device 301, the remote computing devices 314a,b,c, and/or combinations thereof. Thus the software 306 and/or the data 307 can be operational within a cloud computing environment whereby access to the software 306 and/or the data 307 can be performed over the network 315 (e.g., the Internet). Moreover, in an embodiment the data 307 can be synchronized across one or more of the computing device 301, the remote computing devices 314a,b,c, and/or combinations thereof.

An implementation of the software 306 can be stored on or transmitted across some form of computer readable media. Any of the methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The software 306 may be configured to perform some or all steps of the methods disclosed herein. In an embodiment, the software 306 may be configured to determine, based on sequencing a first cell population after infection with a vector comprising a library of at least 3 guide RNAs (gRNAs) for each of a plurality of target regions of DNA, a respective number of gRNAs (n) present for each of the plurality of target regions of DNA, whose read count exceeds a background threshold, determine, based on the respective numbers of gRNAs for each of the plurality of target regions of DNA, a total number of gRNAs (N) present in the first cell population, over all target regions of the plurality of target regions of DNA, whose read count exceeds the background threshold, determine, based on sequencing a second cell population after infection with a vector comprising the library of at least 3 gRNAs for each of the plurality of target regions of DNA, a respective number of gRNAs (n') present for each of the plurality of target regions of DNA, whose read count exceeds the background threshold, determine, based on the respective numbers of gRNAs for each of the plurality of target regions of DNA, a total number of gRNAs (N') present in the second cell population over all target regions of the plurality of target regions of DNA whose read count exceeds the background threshold, determine, for each target region of the plurality of target regions, based on n, N, n', and N', a probability of observing n' gRNAs for the target region in the selected cells by chance, determine, for a target region that comprises a sequence of interest, based on the probability of observing n' gRNAs for the target region in the selected cells by chance, a probability of observing n' or more gRNAs of the sequence of interest in the selected cells by chance, and identify, based on the probability of observing n' or more gRNAs of the sequence of interest in the selected cells by chance, that the sequence of interest is positively selected.

Determining, based on the respective numbers of gRNAs for each of the plurality of target regions of DNA, a total number of gRNAs (N) present in the first cell population, over all target regions of the plurality of target regions of DNA, whose read count exceeds the background threshold can comprise counting each gRNA present in the first cell population whose read count exceeds the background threshold.

Determining, based on the respective numbers of gRNAs for each of the plurality of target regions of DNA, a total number of gRNAs (N') present in the second cell population over all target regions of the plurality of target regions of DNA whose read count exceeds the background threshold can comprise counting each gRNA present in the selected cells of the second cell population whose read count exceeds the background threshold.

Determining, for each target region of the plurality of target regions, based on n, N, n', and N', the probability of observing n' guides for the target region in the selected cells by chance can comprise evaluating $$\frac{\binom{n'}{n} \cdot \binom{N'-n'}{N-n}}{\binom{N'}{N}}, \text{ wherein } \binom{x}{y} = \frac{y!}{x!(y-x)!}$$

computes a number of ways of choosing x objects out of y objects.

Determining, for a target region that comprises a sequence of interest, based on the probability of observing n' guides for the target region in the selected cells by chance, a probability of observing n' or more gRNAs of the sequence of interest in the selected cells by chance can comprise evaluating $$\sum_{i=n'}^{n} \frac{\binom{i}{n} \cdot \binom{N'-i}{N-n}}{\binom{N'}{N}}.$$

Identifying, based on the probability of observing n' or more gRNAs of the sequence of interest in the selected cells by chance, that the sequence of interest is positively selected can comprise determining that the probability of observing n' or more gRNAs of the sequence of interest in the selected cells by chance satisfies a threshold.

The software 306 can be further configured to determine, for each gRNA, an enrichment score. Determining, for each gRNA, an enrichment score can comprise evaluating N/N'.

The software 306 may be configured to store read counts and numbers of gRNAs present as data 307. FIG. 4 illustrates an example data structure 410 representative of an embodiment of the data 307. The data structure 410 may comprise one or more tables, arrays, and the like. The data structure 410 may comprise a plurality of rows and a plurality of columns. The column "Gene #" may contain an identifier of a unique gene or target region of DNA. The column "gRNA per gene" contains the identifiers of the unique gRNAs that may bind to the gene or target region of DNA. The column "gRNA Read Count (Pre-selection)" contains values of the read counts. The column "n" contains the number of gRNAs present per target region (e.g., gene) of DNA derived from the column "gRNA Read Count (Pre-selection)." The column "gRNA Read Count (Post-selection)" contains values of the read counts. The column "n'" contains the number of gRNAs present per target region (e.g., gene) of DNA derived from the column "gRNA Read Count (Post-selection)."

The data structure 410 of FIG. 4 is shown including artificial values stored as data 307 for purposes of illustration. For gene 1, gRNAs A, B, and C are present in the library and may bind to gene 1. After sequencing, gRNAs A, B, and C were present in the cells with read counts of 100, 200, and 10, respectively. The background threshold of 30 may be applied to the read counts and it may be determined by the software 306 that the number of positive occurrences of gRNA's from the library is 2 ($n_1$=3) because only gRNAs A and B have read counts that exceed 30. For gene 2, gRNAs D, E, and F are present in the library and may bind to gene 2. After sequencing, gRNAs D, E, and F were present in the cells with read counts of 500, 300, and 200, respectively. The background threshold of 30 may be applied to the read counts and it may be determined by the software 306 that the number of positive occurrences of gRNA's from the library is 3 ($n_2$=3) because gRNAs D, E, and F have read counts that exceed 30. For gene 3, gRNAs G, H, I, and J are present in the library and may bind to gene 3. After sequencing, gRNAs G, H, I, and J were present in the cells with read counts of 200, 250, 10, and 300, respectively. The background threshold of 30 may be applied to the read counts and it may be determined by the software 306 that the number of positive occurrences of gRNA's from the library is 3 ($n_3$=3) because only gRNAs G, H, and J have read counts that exceed 30. For gene 4, gRNAs K, L, M, and N are present in the library and may bind to gene 4. After sequencing, gRNAs K, L, M, and N were present in the cells with read counts of 100, 200, 200, and 100, respectively. The background threshold of 30 may be applied to the read counts and it may be determined by the software 306 that the number of positive occurrences of gRNA's from the library is 4 ($n_4$=4) because gRNAs K, L, M, and N have read counts that exceed 30.

As shown in the data structure 410 of FIG. 4, the total number of gRNAs, or N, is 12. N is derived from 2+3+3+4 from the values of n for each gene ($n_1+n_2+n_3+n_4$). Accordingly, of the original library of 14 different gRNAs (gRNAs A-N) used to infect the cell population, only 12 different gRNAs were present in a quantity that exceeded the background threshold. The values of n and N may be stored in a data structure. In addition to the values of n and N, the data structure can comprise one or more nucleic acid sequences (e.g., the target region and/or the gRNA sequence) and/or one or more gRNA identifiers.

The column "Gene #" contains an identifier of a unique gene or target region of DNA. The column "gRNA per gene" contains the identifiers of the unique gRNA's that may bind to the gene or target region of DNA. The column "gRNA Read Count (Post-selection)" contains values of the read counts. The column "n'" contains the number of gRNAs present per target region (e.g., gene) of DNA derived from the column "gRNA Read Count (Post-selection)." As shown in the data structure 410 of FIG. 4, for gene 1, gRNAs A, B, and C are present in the library and may bind to gene 1. Post-selection, after sequencing, gRNAs A, B, and C were present (or not present) in the cells with read counts of 0, 50, and 0, respectively. The background threshold of 30 may be applied to the read counts and it may be determined by the software 306 that the number of positive occurrences of gRNA's from the library is 1 ($n'_1=1$) because only gRNA B has a read count that exceeds 30. For gene 2, gRNAs D, E, and F are present in the library and may bind to gene 2. Post-selection, after sequencing, gRNAs D, E, and F were present in the cells with read counts of 100, 100, and 100, respectively. The background threshold of 30 may be applied to the read counts and it may be determined by the software 306 that the number of positive occurrences of gRNA's from the library is 3 ($n'_2=3$) because gRNAs D, E, and F have read counts that exceed 30. For gene 3, gRNAs G, H, I, and J are present in the library and may bind to gene 3. Post-selection, after sequencing, gRNAs G, H, I, and J were present (or not present) in the cells with read counts of 0, 0, 0, and 20, respectively. The background threshold of 30 may be applied to the read counts and it may be determined by the software 306 that the number of positive occurrences of gRNA's from the library is 0 ($n'_3=0$) because no have read counts that exceed 30. For gene 4, gRNAs K, L, M, and N are present in the library and may bind to gene 4. Post-selection, after sequencing, gRNAs K, L, M, and N were present (or not present) in the cells with read counts of 0, 0, 0, and 20, respectively. The background threshold of 30 may be applied to the read counts and it may be determined by the software 306 that the number of positive occurrences of gRNAs from the library is 0 ($n'_4=0$) because no gRNAs have read counts that exceed 30.

A total number of gRNAs, or N', over all target regions, present in the selected cells whose read count exceeds the background threshold can be determined by the software 306. As shown in the data structure 410 of FIG. 4, the total number of gRNAs, or N', is 4. N' is derived from 1+3+0+0 from the values of n for each gene ($n'_1+n'_2+n'_3+n'_4$). Accordingly, of the original library of 14 different gRNAs (gRNAs A-N) used to infect the cell population, only 4 different gRNAs were present in the selected cells in a quantity that exceeded the background threshold. The values of n' and N' may be stored in a data structure. In addition to the values of n' and N', the data structure can comprise one or more nucleic acid sequences (e.g., the target region and/or the gRNA sequence) and/or one or more gRNA identifiers.

In an embodiment, the data 307 may also be configured to store one or more results of the software 306. FIG. 5 shows an example result data structure 510 generated by the software 306, for example, using the data structure 410 as input. The data structure 510 may comprise one or more tables, arrays, and the like. FIG. 5 shows artificial data and artificial results for purposes of illustration. Formal statistical p-values may be calculated for positively observing a number of guides over experiment repeats given the library size, number of guides per gene, and the total number of positive guides in each experiment. The data structure 510 indicates an initial library of 63,950 gRNAs (N). The data structure 510 indicates that after selection, 4,946 gRNAs (N') (number of unique gRNAs, not quantity of gRNAs) remained in the cell population of experiment 1 and 13,606 gRNAs (N') (number of unique gRNAs, not quantity of gRNAs) remained in the cell population of experiment 2. As shown in the data structure 510, target region 1 has three (3) gRNAs capable of binding to at least a portion of target region 1. For experiment 1, the probability that 3 out of the 3 gRNAs are present by chance in the post-selection cell population, given that 4,946 gRNAs remained in the cell population after selection, is 0.000462378. For experiment 2, the probability that 3 out of the 3 gRNAs are present by chance in the post-selection cell population, given that 13,606 gRNAs remained in the cell population after selection, is 0.009629. The data structure 510 indicates the results for the probabilities that 2 out of the 3, 1 out of the 3, and 0 out of the 3 gRNAs are present by chance in the post-selection cell population.

As shown the data structure 510, target region 2 has four (4) gRNAs capable of binding to at least a portion of target region 2. The data structure 510 indicates the results for the probabilities that 4 out of the 4, 3 out of the 4, 2 out of the 4, 1 out of the 4, and 0 out of the 4 gRNAs are present by chance in the post-selection cell population. From the results shown in the data structure 510, it may be determined by the software 306 that a probability is below a threshold (e.g., sufficiently small). For example, for target region 2, experiment 1, the probability that the 4 out of the 4 gRNAs were present by chance is 3.57411E-05, indicating that it is likely that the 4 out of the 4 gRNAs are not merely present by chance.

EXAMPLES

A. Example 1. Development of Genome-Wide CRISPR/Cas9 Screening Platform to Identify Genetic Modifiers of Tau Aggregation To identify genes and pathways that modify the processes of abnormal tau protein aggregation, a platform was developed for performing genome-wide screens with CRISPR nuclease (CRISPRn) sgRNA libraries to identify genes that regulate the potential of cells to be "seeded" by tau disease-associated protein aggregates (i.e. genes which, when disrupted, cause cells to be more susceptible to tau aggregate formation when exposed to a source of tau fibrillized protein). The screen employed a tau biosensor human cell line consisting of HEK293T cells stably expressing tau four-repeat domain, tau_4RD, comprising the tau microtubule binding domain (MBD) with the P301S pathogenic mutation, fused to either CFP or YFP. That is, the HEK293T cell lines contain two transgenes stably expressing disease-associated protein variants fused to the fluorescent protein CFP or the fluorescent protein YFP: tau4RD-CFP/tau4RD-YFP (TCY), wherein the tau repeat domain (4RD) comprises the P301S pathogenic mutation.

In these biosensor lines, tau-CFP/tau-YFP protein aggregation produces a FRET signal, the result of a transfer of fluorescent energy from donor CFP to acceptor YFP. FRET-positive cells, which contain tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal. Aggregate-containing cells can be isolated by FACS. Stably propagating aggregate-containing cell lines, Agg[+], can be isolated by clonal serial dilution of Agg[−] cell lines.

Several modifications were made to this tau biosensor cell line to make it useful for genetic screening. First, these tau biosensor cells were modified by introducing a Cas9-expressing transgene (SpCas9) via a lentiviral vector. Clonal transgenic cell lines expressing Cas9 were selected with blasticidin and isolated by clonal serial dilution to obtain single-cell-derived clones. Clones were evaluated for level of Cas9 expression by qRT-PCR and for DNA cleavage activity by digital PCR.

Specifically, Cas9 mutation efficiency was assessed by digital PCR 3 and 7 days after transduction of lentiviruses encoding gRNAs against two selected target genes. Cutting efficiency was limited by Cas9 levels in lower-expressing clones. A clone with an adequate level of Cas9 expression was needed to achieve maximum activity. Several derived clones with lower Cas9 expression were not able to cut target sequences efficiently, whereas clones with higher expression (including those used for screening) were able to generate mutations at target sequences in the genes PERK and SNCA with approximately 80% efficiency after three days in culture. Efficient cutting was observed already at 3 days after gRNA transduction with only marginal improvement after 7 days. Clone 7B10-C3 was selected as a high-performing clone to use for subsequent library screens.

Second, reagents and a method were developed for sensitizing cells to tau seeding activity. Tau cell-to-cell propagation may result from tau aggregation activity secreted by aggregate-containing cells. To study cell propagation of tau aggregation, sub-clones were obtained of a tau-YFP cell line consisting of HEK293T cells stably expressing tau repeat domain, tau_4RD, comprising the tau microtubule binding domain (MBD) with the P301S pathogenic mutation, fused to YFP.

Cells in which tau-YFP protein stably presents in an aggregated state (Agg[+]) were obtained by treating these tau-YFP cells with recombinant fibrillized tau mixed with lipofectamine reagent in order to seed the aggregation of the tau-YFP protein stably expressed by these cells. The "seeded" cells were then serially diluted to obtain single-cell-derived clones. These clones were then expanded to identify clonal cell lines in which tau-YFP aggregates stably persist in all cells with growth and multiple passages over time. One of these tau-YFP_Agg[+] clones was used to produce conditioned medium by collecting medium that has been on confluent tau-YFP_Agg[+] cells for four days. Conditioned medium (CM) was then applied onto naïve biosensor tau-CFP/Tau-YFP cells at a ratio of 3:1 CM:fresh medium so that tau aggregation could be induced in a small percentage of these recipient cells. No lipofectamine was used. Lipofectamine was not used in order to have an assay that is as physiologic as possible, without tricking the recipient cells to force/increase tau aggregation using lipofectamine. As measured by using flow cytometry to assess the percentage of cells producing a FRET signal as a measure of aggregation, conditioned medium consistently induced FRET in approximately 0.1% of cells.

B. Example 2. Genome-Wide CRISPR/Cas9 Screening to Identify Genetic Modifiers of Tau Aggregation To reveal modifier genes of tau aggregation as enriched sgRNAs in FRET(+) cells, the Cas9-expressing tau-CFP/tau-YFP biosensor cells without aggregates (Agg[−]) were transduced with two human genome-wide CRISPR sgRNA libraries (GeCKO A and GeCKO B) (FIG. 7) using a lentiviral delivery approach to introduce knock-out mutations at each target gene. Each CRISPR sgRNA library targets 5′ constitutive exons for functional knock-out with an average coverage of ~3 sgRNAs per gene (total of 6 gRNAs per gene in the two libraries combined). Read count distribution (i.e., the representation of each gRNA in the library) was normal and similar for each library. The sgRNAs were designed to avoid off-target effects by avoiding sgRNAs with two or fewer mismatches to off-target genomic sequences. The libraries cover 19,050 human genes and 1864 miRNA with 1000 non-targeting control sgRNAs. The libraries were transduced at a multiplicity of infection (MOI) <0.3 at a coverage of >300 cells per sgRNA. Tau biosensor cells were grown under puromycin selection to select cells with integration and expression of a unique sgRNA per cell. Puromycin selection began 24 h after transduction at 1 µg/mL. Five independent screening replicates were used in the primary screen.

Samples of the full, transduced cell population were collected upon cell passaging at Day 3 and Day 6 post-transduction. After the Day 6 passage, cells were grown in conditioned medium to sensitize them to the seeding activity. At Day 10, fluorescence-assisted cell sorting (FACS) was used to isolate specifically the sub-population of FRET [+] cells. The screening consisted of five replicated experiments. DNA isolation and PCR amplification of the integrated sgRNA constructs allowed a characterization by next generation sequencing (NGS) of the sgRNA repertoire at each time point.

Statistical analysis of the NGS data enabled identification of sgRNAs enriched in the Day 10 FRET[+] sub-population of the five experiments as compared to the sgRNAs repertoire at earlier time points Day 3 and Day 6. The first strategy to identify potential tau modifiers was to use DNA sequencing to produce sgRNA read counts in each sample using the DESeq algorithm to find the sgRNAs that are more abundant in Day 10 vs. Day 3 or Day 10 vs. Day 6 but not in Day 6 vs. Day 3 (fold change (fc)≥1.5 and negative binomial test p<0.01). Fc≥1.5 means the ratio of (average of day 10 counts)/(average of day 3 or day 6 counts)≥1.5. P<0.01 means the chance that there is no statistical difference between Day 10 and Day 3 or Day 6 counts<0.01. The DESeq algorithm is a widely used algorithm for "differential expression analysis for sequence count data." See, e.g., Anders et al. (2010) Genome Biology 11:R106, herein incorporated by reference.

Specifically, two comparisons were used in each library to identify the significant sgRNAs: Day 10 vs. Day 3, and Day 10 vs. Day 6. For each of these four comparisons, the DESeq algorithm was used, and the cutoff threshold to be considered as significant was fold change≥1.5 as well as negative binomial test p<0.01. Once the significant guides were identified in each of these comparisons for each library, a gene was considered to be significant if it meets one of the two following criteria: (1) at least two sgRNAs corresponding to the that gene were considered to be significant in one comparison (either Day 10 vs. Day 3 or Day 10 vs. Day 6); and (2) at least one sgRNA was significant in both comparisons (Day 10 vs. Day 3 and Day 10 vs. Day 6). Using this algorithm, five genes were identified as significant from the first library and four genes from the second library. See Table 1.

TABLE 1

Genes Identified Using Strategy #1.

| Day 10 vs Day 3 | | Day 10 vs Day 6 | | Day 6 vs Day 3 | |
|---|---|---|---|---|---|
| Gene | Significant gRNAs | Gene | Significant gRNAs | Gene | Significant gRNAs |
| Library #1 | | | | | |
| Target Gene 1 | 1 | Target Gene 1 | 1 | Target Gene 1 | 0 |
| Target Gene 2 | 3 | Target Gene 2 | 1 | Target Gene 2 | 0 |
| Target Gene 15 | 1 | Target Gene 15 | 1 | Target Gene 15 | 0 |
| Target Gene 16 | 1 | Target Gene 16 | 1 | Target Gene 16 | 0 |
| Target Gene 17 | 2 | Target Gene 17 | 0 | Target Gene 17 | 0 |
| Library #2 | | | | | |
| Target Gene 2 | 1 | Target Gene 2 | 1 | Target Gene 2 | 0 |
| Target Gene 18 | 1 | Target Gene 18 | 1 | Target Gene 18 | 0 |
| Target Gene 19 | 1 | Target Gene 19 | 1 | Target Gene 19 | 0 |
| Target Gene 20 | 1 | Target Gene 20 | 1 | Target Gene 20 | 0 |

However, this first strategy requires certain levels of read count homogeneity within each experiment group might be too stringent. For the same sgRNA, many factors could produce read count variability among the samples within each experiment group (Day 3, Day 6 or Day 10 samples), such as initial viral counts in the screening library, infection or gene editing efficiency, and relative growth rate post-gene editing. Thus, a second strategy was also used based on the positive occurrence (read count>30) of guides per gene in each sample at Day 10 (post-selection) instead of exact read count.

The pre-selection CRISPR experiment was repeated four times. As shown in FIG. 6, for gene "G1" in pre-selection experiment "Exp1," gRNAs "g1," "g2," and "g3" were present in the cell population with read counts of 121, 1000, and 302, respectively. For gene "G2," gRNAs "g4," "g5," "g6," and "g7" were present in the cell population with read counts of 443, 2012, 534, and 150, respectively. Such read count data is generated for genes "G1" through genes "G21,000." For each gene, a "sum of presence," or n, was determined. The "sum of presence," or the respective numbers of gRNAs present per target region of DNA, was determined by comparing the individual read counts of each gRNA to a background threshold. In this instance, 30 was used as the background threshold. Accordingly, the "sum of presence" indicates the number of gRNAs being qualitatively present, in contrast with the quantity of gRNAs present which is indicated by the read counts. The sum of presence of gRNAs corresponding to gene G1 is 3 because the read counts for gRNA g1, g2, and g3 each exceeds the background threshold of 30. The sum of presence of gRNAs corresponding to gene G2 is 4 because the read counts for gRNA g4, g5, g6, and g7 each exceeds the background threshold of 30. The total number of gRNAs, or N, over all target regions, present in the cell population whose read count exceeds the background threshold is indicated as 59,010. Accordingly, of the original library of approximately 64,000 different gRNAs used to infect the cell population, only approximately 59,000 different gRNAs were present in a quantity that exceeded the background threshold.

The CRISPR experiment with phenotypic selection was repeated four times. However, prior to sequencing, cells in the cell population were sorted according to phenotype using fluorescence techniques (e.g., FRET fluorescence). If Cas9/CRISPR cuts a target region (e.g., a gene) of a cell and the cell did not fluoresce, the gene was successfully knocked out. If the cell fluoresces, then the gene was not knocked out. The fluorescing cells can then be sequenced, the non-fluorescing cells were not sequenced. The selected cells represent cells that exhibit a specific phenotype/marker.

As shown in FIG. 6 for gene "G1" in post-selection experiment "Exp1" gRNAs "g1," "g2," and "g3" were present (or not present) in the cell population with read counts of 0, 8, and 12, respectively. For gene "G2," gRNAs "g4," "g5," "g6," and "g7" were present (or not present) in the cell population with read counts of 4, 25, 4, and 150, respectively. Such read count data is generated for genes "G1" through genes "G21,000." For each gene, a "sum of presence," or n', was determined. The "sum of presence," or the respective numbers of gRNAs present per target region of DNA, was determined by comparing the individual read counts of each gRNA to a background threshold. In this instance, 30 was used as the background threshold. Accordingly, the "sum of presence" indicates the number of gRNAs present, in contrast with the quantity of gRNAs present which is indicated by the read counts. The sum of presence of gRNAs corresponding to gene G1 is 0 because the read counts for gRNA g1, g2, and g3 each fails to exceed the background threshold of 30. The sum of presence of gRNAs corresponding to gene G2 is 1 because only the read count for gRNA g7 exceeded the background threshold of 30. The total number of gRNAs, or N', over all target regions, present in the cell population whose read count exceeded the background threshold is indicated as 4,320. Accordingly, of the original library of approximately 64,000 different gRNAs used to infect the cell population, only approximately 4,320 different gRNAs were present in a quantity that exceeded the background threshold.

A formal statistical p-value was calculated for positively observing a number of guides in the post-selection sample given the library size, number of guides per gene, and the total number of positive guides in the post-selection sample. Once the read counts have been accounted for, the probability of observing n' guides for a target region (e.g., a gene) in the selected cells (post-selection) by chance was determined according to the formula $$\frac{\binom{n'}{n} \cdot \binom{N'-n'}{N-n}}{\binom{N'}{N}}.$$

By way of explanation, $$\binom{x}{y} = \frac{y!}{x!(y-x)!},$$

which determines a number of ways of choosing x objects out of y objects.

Once the probability of observing n' guides for the target region (e.g., a gene) in the selected cells (post-selection) by chance was determined, the probability of observing n' or more gRNAs of the gene in the selected cells (post-selection) by chance was determined according to the formula $$\sum_{i=n'}^{n} \frac{\binom{i}{n} \cdot \binom{N'-i}{N-n}}{\binom{N'}{N}}.$$

Once the probability of observing n' or more gRNAs of the target region in the selected cells (post-selection) by chance was determined, the average enrichment gRNAs was determined at the target region level. The overall enrichment of read counts of a gene post-selection compared to pre-selection was used as additional parameter to identify positive genes. The average enrichment was represented by an enrichment score. The enrichment score was determined by evaluating N/N'. Taken from FIG. 6, the enrichment score is 59010/4320, or 13.66.

The probability of observing n' or more gRNAs of the target region in the selected cells (post-selection) by chance may be used to assess whether the target region is positively selected. The enrichment score may additionally be used to assess whether the target region is positively selected. Target regions with a probability of observing n' or more gRNAs of the target region in the selected cells that is significantly below the probability of observing n' or more gRNAs of the target region in the selected cells (post-selection) by chance may be identified as positively selected target regions. Additionally, a target region having an enrichment score above a threshold may indicate a positively selected target region.

This second strategy thus represents a new and more sensitive analysis method for CRISPR positive selection. The goal of CRISPR positive selection is to use DNA sequencing to identify genes for which perturbation by sgRNAs is correlated to the phenotype. To reduce the noise background, multiple sgRNAs for the same gene together with experiment replicates are usually used in these experiments. However, currently the commonly used statistical analysis methods, which require a certain degree of homogeneity/agreement among the sgRNAs for the same gene as well as among technical repeats, do not work well. This is because these methods cannot handle huge variation among sgRNAs and repeats for the same gene, due to many possible reasons (e.g., different infection or gene editing efficiency, initial viral counts in the screening library, and the presence of other sgRNAs with the same phenotype). In contrast, the method shown in this Example is robust to large variations. It is based on the positive occurrences of guides per gene in an individual experiment instead of the exact read count of each sgRNA. Formal statistical p-values are calculated for positively observing a number of sgRNAs over experiment repeats given the library size, number of sgRNAs per gene, and the totally number of positive sgRNAs in each experiment. Relative sgRNA sequence read enrichment before and after phenotype selection is also used as a parameter. This method performs better than widely used methods up-to-date, including DESeq, MAGECK, and others. Specifically, this method includes the following steps:

(1) For each experiment, identifying any present guides in cells with positive phenotype.

(2) At the gene level, calculating the random chance of guides being present (aka p-value) in each experiment. The overall chance of being present across multiple experiments is calculated by Fisher's combined probability test (reference: Fisher, R. A.; Fisher, R. A (1948). "Questions and answers #14". The American Statistician). That is, first computing a test statistic $\phi$ using the p-values from the multiple experiments: $\phi = -2\Sigma_{k=1}^{K} p_k$, where $p_k$ is the p-value calculated for the kth experiment and K is the total number of the experiments. Then the combined the p-value over the K experiments is equal to the probability of observing the value of $\phi$ under the chi-square distribution with the degree of freedom of 2*K.

(3) Calculating the average enrichment of guides at gene level: Enrichment score=relative abundance post-selection/relative abundance pre-selection. Relative abundance=read count of guides for a gene/read count of all guides.

(4) Selecting genes significantly below the random chance of being present as well as above certain enrichment score.

C. Example 3

CRISPR/Cas9 activating and inactivating mutagenesis was used to screen for genetic modifiers of Tau and α-synuclein fibrillization and propagation using CRISPRn sgRNA libraries (hGeCKO-A and hGeCKO-B) targeting coding exons for functional knock-out. FIG. 7 shows sample identifiers, experiment numbers, time until sequencing, and identifies which library (Gecko A or Gecko B) was used for the experiment.

The Gecko A library was comprised of approximately 63,950 gRNAs. Of the 63,950 gRNAs, 56,116 gRNAs targeted 18,874 genes, with the majority of genes being targeted by 3 gRNAs. Of the 63,950 gRNAs, 6,834 gRNAs targeted 1,795 micoRNA, with the majority of microRNA being targeted by 4 gRNAs.

The Gecko B library was comprised of approximately 56,869 gRNAs. Of the 56,869 gRNAs, 55,869 gRNAs targeted 18,834 genes, with the majority of genes being targeted by 3 gRNAs. Of the 56,869 gRNAs, no gRNAs targeted micoRNA. Of the 1,000 gRNAs had no target.

At Day 3 and Day 6, no phenotype was exhibited. At Day 10, samples were phenotype positive.

Figure 8:
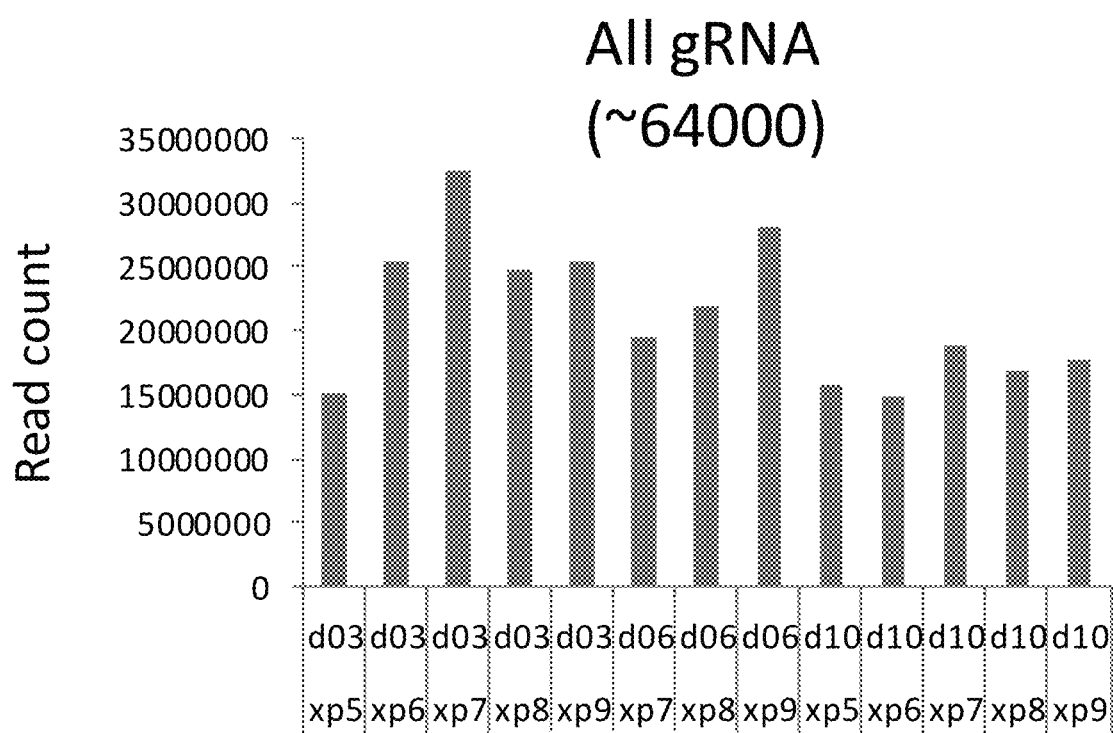
FIG. 8 shows the read count prior to normalization for each gRNA from the Gecko A library used in each experiment (xp #) over days 3, 6, and 10, whereby the gRNA were used to direct inactivation of the target.

FIG. 8 shows DNA read counts from the samples infected with the Gecko A library. Each bar represents a sample infected by a virus. Each sample was sequenced at Day 3 (d03), Day 6 (d06), or Day 10 (d10), and each sample represents a sequencing readout for the gRNAs, rather than the whole genome.

FIG. 9 shows normalization of the read counts from the samples infected with the Gecko A library to the median. Normalization was performed by dividing a gRNA read count by the sum of read counts in each sample and divided multiplied by the median of the sum of the read counts over all samples. The bottom bar graph is qualitative and indicates read counts above the threshold of 30; day 10 is post-selection. Given a similar sum of read count, day 3 and day 6 samples had a large variety of gRNAs, while Day 10 samples had much less variety of gRNAs.

FIG. 10 shows the formal statistical p-values that were calculated for positively observing a number of gRNAs over experiment repeats given the library size, number of gRNAs per gene, and the total number of positive gRNAs in each experiment. The p-values are shown for five samples infected with the Gecko A library and sequenced at Day 10.

EMBODIMENTS

Embodiment 1. A method comprising:
(A) infecting a first culture of cas9-positive cells with a library of viral vectors, the library comprising at least 3 guide RNAs (gRNAs) for cleaving a target region of DNA within the genome of the cells; sequencing the cells to obtain a read count for each of the gRNAs;
summing ($\Sigma$) respective numbers of gRNAs, per target region of DNA, whose read count exceeds a background threshold, wherein $\Sigma=n$; and summing ($\Sigma$) a total number of gRNAs, over all target regions, whose read count exceeds the background threshold, wherein $\Sigma=N$;
(B) infecting a second culture of cas9-positive cells with the library of viral vectors;
categorizing the cells of the second culture as either having a designated phenotype or not having the designated phenotype; selecting cells having the designated phenotype and sequencing the selected cells to obtain a post-selection read count for each of the gRNAs;
summing ($\Sigma$) respective numbers of gRNAs, per target region of DNA, in the selected cells whose post-selection read count exceeds the background threshold, wherein $\Sigma=n'$; and
summing ($\Sigma$) a total number of gRNAs, over all target regions, of the selected cells whose read count exceeds the threshold, wherein $\Sigma=N'$; (C) calculating, for a target region of DNA, a probability of observing n' gRNAs for the target region in the selected cells by chance according to the formula $$\frac{\binom{n'}{n}\cdot\binom{N'-n'}{N-n}}{\binom{N'}{N}}, \text{ wherein } \binom{x}{y}=\frac{y!}{x!\,(y-x)!}$$

computes a number of ways of choosing x objects out of y objects; and calculating, for a target region of DNA that comprises a gene, a probability of observing n' or more gRNAs of the gene in the selected cells by chance according to the formula $$\sum_{i=n'}^{n}\frac{\binom{i}{n}\cdot\binom{N'-i}{N-n}}{\binom{N'}{N}}.$$

Embodiment 2. A method comprising:
(A) infecting a first culture of cas9-positive cells with a library of viral vectors, the library comprising at least 3 guide RNAs (gRNAs) for enhancing transcription of a target region of DNA within the genome of the cells;
sequencing the cells to obtain a read count for each of the gRNAs;
summing ($\Sigma$) respective numbers of gRNAs, per target region of DNA, whose read count exceeds a background threshold, wherein $\Sigma=n$; and
summing ($\Sigma$) a total number of gRNAs, over all target regions, whose read count exceeds the background threshold, wherein $\Sigma=N$;
(B) infecting a second culture of cas9-positive cells with the library of viral vectors;
categorizing the cells of the second culture as either having a designated phenotype or not having the designated phenotype;
selecting cells having the designated phenotype and sequencing the selected cells to obtain a post-selection read count for each of the gRNAs;
summing ($\Sigma$) respective numbers of gRNAs, per target region of DNA, in the selected cells whose post-selection read count exceeds the background threshold, wherein $\Sigma=n'$; and
summing ($\Sigma$) a total number of gRNAs, over all target regions, of the selected cells whose read count exceeds the threshold, wherein $\Sigma=N'$;
(C) calculating, for a target region of DNA, a probability of observing n' gRNAs for the target region in the selected cells by chance according to the formula $$\frac{\binom{n'}{n}\cdot\binom{N'-n'}{N-n}}{\binom{N'}{N}}, \text{ wherein } \binom{x}{y}=\frac{y!}{x!\,(y-x)!}$$

computes a number of ways of choosing x objects out of y objects; and
calculating, for a target region of DNA that comprises a gene, a probability of observing n' or more gRNAs of the gene in the selected cells by chance according to the formula $$\sum_{i=n'}^{n}\frac{\binom{i}{n}\cdot\binom{N'-i}{N-n}}{\binom{N'}{N}}.$$

Embodiment 3. The method of any preceding embodiment, wherein the first culture is infected according to a CRISPR technique.
Embodiment 4. The method of any preceding embodiment, wherein the cas-9 positive cells of the first culture are modified to contain one or more selectable markers.
Embodiment 5. The method of any preceding embodiment, wherein the designated phenotype is fluorescence.
Embodiment 6. The method of any preceding embodiment, wherein the designated phenotype is cell survival.
Embodiment 7. The method of embodiment 4, wherein the one or more selectable markers comprise a fluorescent marker.
Embodiment 8. The method of embodiment 7, wherein the fluorescent marker is part of a FRET biosensor.
Embodiment 9. The method of embodiment 4, wherein the one or more selectable markers is a detectable enzyme.
Embodiment 10. The method of embodiment 9, wherein the detectable enzyme is β-galactosidase.
Embodiment 11. The method of embodiment 9, wherein the detectable enzyme is luciferase.

Embodiment 12. The method of any preceding embodiment, wherein a target region comprises a gene.

Embodiment 13. The method of any preceding embodiment, wherein categorizing cells of the second culture as either having the designated phenotype or not having the designated phenotype comprises applying a selection mechanism to the second cell culture.

Embodiment 14. The method of embodiment 13, wherein the selection mechanism comprises one or more of exposing the second cell population to a drug or exposing the second cell population to a substance that identifies protein activity or expression levels.

Embodiment 15. The method of embodiment 4, wherein selecting cells having the designated phenotype comprises sorting the cells based on the one or more selectable markers.

Embodiment 16. The method of any preceding embodiment, further comprising identifying, based on the probability of observing n' or more gRNAs of the gene in the selected cells by chance, that the target region is positively selected.

Embodiment 17. The method of embodiment 16, wherein identifying that the target region is positively selected comprises determining that the probability of observing n' or more gRNAs of the sequence of interest in the selected cells by chance satisfies a threshold.

Embodiment 18. The method of any preceding embodiment, further comprising determining, for each gRNA, an enrichment score.

Embodiment 19. The method of embodiment 18, wherein determining, for each gRNA, the enrichment score comprises evaluating N/N'.

Embodiment 20. The method of any of embodiments 2-19, wherein the cas-9 positive cells comprise deactivated cas-9.

Embodiment 21. The method of embodiment 20, wherein the deactivated cas-9 is fused to at least one transcription activation domain.

Embodiment 22. The method of any preceding embodiment, wherein the target region of DNA regulates a downstream gene or protein.

Embodiment 23. The method of embodiment 22, wherein regulating a downstream gene or protein comprises the activation or inhibition of the downstream gene or protein.

Embodiment 24. The method of any preceding embodiment, further comprising identifying, based on the probability of observing n' or more gRNAs of the gene in the selected cells by chance, the target region as a modifier of a second gene.

Embodiment 25. The method of any preceding embodiment, further comprising identifying, based on the probability of observing n' or more gRNAs of the gene in the selected cells by chance, the target region as a therapeutic target.

Embodiment 26. The method of any preceding embodiment, further comprising identifying, based on the probability of observing n' or more gRNAs of the gene in the selected cells by chance, the target region as correlated with the designated phenotype.

Embodiment 27. The method of any preceding embodiment, further comprising identifying, based on the probability of observing n' or more gRNAs of the gene in the selected cells by chance, the target region as exhibiting a protective effect.

Embodiment 28. A method comprising: determining, based on sequencing a first cell population after infection with a vector comprising a library of at least 3 guide RNAs (gRNAs) for each of a plurality of target regions of DNA, a respective number of gRNAs (n) present for each of the plurality of target regions of DNA, whose read count exceeds a background threshold; determining, based on the respective numbers of gRNAs for each of the plurality of target regions of DNA, a total number of gRNAs (N) present in the first cell population, over all target regions of the plurality of target regions of DNA, whose read count exceeds the background threshold; determining, based on sequencing a second cell population after infection with a vector comprising the library of at least 3 gRNAs for each of the plurality of target regions of DNA, a respective number of gRNAs (n') present for each of the plurality of target regions of DNA, whose read count exceeds the background threshold;
determining, based on the respective numbers of gRNAs for each of the plurality of target regions of DNA, a total number of gRNAs (N') present in the second cell population over all target regions of the plurality of target regions of DNA whose read count exceeds the background threshold; determining, for each target region of the plurality of target regions, based on n, N, n', and N', a probability of observing n' gRNAs for the target region in the selected cells by chance; determining, for a target region that comprises a sequence of interest, based on the probability of observing n' gRNAs for the target region in the selected cells by chance, a probability of observing n' or more gRNAs of the sequence of interest in the selected cells by chance; and identifying, based on the probability of observing n' or more gRNAs of the sequence of interest in the selected cells by chance, that the sequence of interest is positively selected.

Embodiment 29. The method of embodiment 28, wherein the first cell population and the second population comprise cas-9 positive cells.

Embodiment 30. The method of embodiment 29, wherein determining, based on sequencing a first cell population after infection with a vector comprising a library of at least 3 gRNAs for each of a plurality of target regions of DNA, a respective number of gRNAs (n) present for each of the plurality of target regions of DNA, whose read count exceeds a background threshold comprises: infecting the first cell population with the library of viral vectors; sequencing cells of the first cell population to obtain a read count for each of the gRNAs; and counting, for each of the plurality of target regions of DNA, each gRNA whose read count exceeds the background threshold.

Embodiment 31. The method of embodiment 30, wherein determining, based on the respective numbers of gRNAs for each of the plurality of target regions of DNA, a total number of gRNAs (N) present in the first cell population, over all target regions of the plurality of target regions of DNA, whose read count exceeds the background threshold comprises counting each gRNA present in the first cell population whose read count exceeds the background threshold.

Embodiment 32. The method of embodiment 31, wherein determining, based on sequencing a second cell population after infection with a vector comprising the library of at least 3 gRNAs for each of the plurality of target regions of DNA, a respective number of gRNAs (n') present for each of the plurality of target regions of DNA, whose read count exceeds the background threshold comprises: categorizing cells of the second cell population as either having a designated phenotype or not having the designated phenotype;
selecting cells having the designated phenotype; sequencing the selected cells to obtain a read count for each of the gRNAs; and counting, for each of the plurality of target regions of DNA, each gRNA whose read count exceeds the background threshold.

Embodiment 33. The method of any one of embodiments 28-32, wherein determining, based on the respective numbers of gRNAs for each of the plurality of target regions of DNA, a total number of gRNAs (N') present in the second cell population over all target regions of the plurality of target regions of DNA whose read count exceeds the background threshold comprises counting each gRNA present in the selected cells of the second cell population whose read count exceeds the background threshold.

Embodiment 34. The method of any one of embodiments 28-33, wherein determining, for each target region of the plurality of target regions, based on n, N, n', and N', the probability of observing n' gRNAs for the target region in the selected cells by chance comprises evaluating $$\frac{\binom{n'}{n} \cdot \binom{N'-n'}{N-n}}{\binom{N'}{N}}, \text{ wherein } \binom{x}{y} = \frac{y!}{x!(y-x)!}$$

computes a number of ways of choosing x objects out of y objects.

Embodiment 35. The method of any one of embodiments 28-34, wherein determining, for a target region that comprises a sequence of interest, based on the probability of observing n' gRNAs for the target region in the selected cells by chance, a probability of observing n' or more gRNAs of the sequence of interest in the selected cells by chance comprises evaluating $$\sum_{i=n'}^{n} \frac{\binom{i}{n} \cdot \binom{N'-i}{N-n}}{\binom{N'}{N}}.$$

Embodiment 36. The method of any one of embodiments 28-35, wherein identifying, based on the probability of observing n' or more gRNAs of the sequence of interest in the selected cells by chance, that the sequence of interest is positively selected comprises determining that the probability of observing n' or more gRNAs of the sequence of interest in the selected cells by chance satisfies a threshold.

Embodiment 37. The method of any one of embodiments 28-36, further comprising determining, for each gRNA, an enrichment score.

Embodiment 38. The method of embodiment 37, wherein determining, for each gRNA, an enrichment score comprises evaluating N/N'.

Embodiment 39. The method of any one of embodiments 28-38, wherein the cas-9 positive cells comprise deactivated cas-9.

Embodiment 40. The method of embodiment 39, wherein the deactivated cas-9 is fused to at least one transcription activation domain.

Embodiment 41. An apparatus comprising: one or more processors; and memory storing processor executable instructions that, when executed by the one or more processors, cause the apparatus to: (A) receive first read count data, wherein the first read count data was generated by, infecting a first culture of cas9-positive cells with a library of viral vectors, the library comprising at least 3 guide RNAs (gRNAs) for cleaving a target region of DNA within the genome of the cells, and sequencing the cells to obtain a read count for each of the gRNAs; sum ($\Sigma$), based on the first read count data, respective numbers of gRNAs, per target region of DNA, whose read count exceeds a background threshold, wherein $\Sigma$=n; and sum ($\Sigma$), based on the first read count data, a total number of gRNAs, over all target regions, whose read count exceeds the background threshold, wherein $\Sigma$=N; (B) receive second read count data, wherein the second read count data was generated by, infecting a second culture of cas9-positive cells with the library of viral vectors, categorizing the cells of the second culture as either having a designated phenotype or not having the designated phenotype, and selecting cells having the designated phenotype and sequencing the selected cells to obtain a post-selection read count for each of the gRNAs; sum ($\Sigma$), based on the second read count data, respective numbers of gRNAs, per target region of DNA, in the selected cells whose post-selection read count exceeds the background threshold, wherein $\Sigma$=n'; and sum ($\Sigma$), based on the second read count data, a total number of gRNAs, over all target regions, of the selected cells whose read count exceeds the threshold, wherein $\Sigma$=N'; (C) calculate, for a target region of DNA, a probability of observing n' gRNAs for the target region in the selected cells by chance according to the formula $$\frac{\binom{n'}{n} \cdot \binom{N'-n'}{N-n}}{\binom{N'}{N}}, \text{ wherein } \binom{x}{y} = \frac{y!}{x!(y-x)!}$$

computes a number of ways of choosing x objects out of y objects; and calculate, for a target region of DNA that comprises a gene, a probability of observing n' or more gRNAs of the gene in the selected cells by chance according to the formula $$\sum_{i=n'}^{n} \frac{\binom{i}{n} \cdot \binom{N'-i}{N-n}}{\binom{N'}{N}}.$$

Embodiment 42. The apparatus of embodiment 41, wherein the first culture is infected according to a CRISPR technique.

Embodiment 43. The apparatus of any one of embodiments 41-42, wherein the cas-9 positive cells of the first culture are modified to contain one or more selectable markers.

Embodiment 44. The apparatus of any one of embodiments 41-43, wherein a target region comprises a gene.

Embodiment 45. The apparatus of any one of embodiments 41-44, wherein categorizing cells of the second culture as either having the designated phenotype or not having the designated phenotype comprises applying a selection mechanism to the second cell culture.

Embodiment 46. The apparatus of embodiment 45, wherein the selection mechanism comprises one or more of exposing the second cell population to a drug or exposing the second cell population to a substance that identifies protein activity or expression levels.

Embodiment 47. The apparatus of any one of embodiments 41-46, wherein selecting cells having the designated phenotype comprises sorting the cells based on the one or more selectable markers.

Embodiment 48. The apparatus of any one of embodiments 41-47, further comprising identifying, based on the probability of observing n' or more gRNAs of the gene in the selected cells by chance, that the target region is positively selected.

Embodiment 49. The apparatus of embodiment 48, wherein identifying that the target region is positively selected comprises determining that the probability of observing n' or more gRNAs of the sequence of interest in the selected cells by chance satisfies a threshold.

Embodiment 50. The apparatus of any one of embodiments 41-49, further comprising determining, for each gRNA, an enrichment score.

Embodiment 51. The apparatus of embodiment 50, wherein determining, for each gRNA, the enrichment score comprises evaluating N/N'.

Embodiment 52. The apparatus of any one of embodiments 41-51, wherein the cas-9 positive cells comprise deactivated cas-9.

Embodiment 53. The apparatus of embodiment 52, wherein the deactivated cas-9 is fused to at least one transcription activation domain.

Embodiment 54. A non-transitory computer readable medium for determining a probability of observing one or more guide RNA (gRNA) by chance, the non-transitory computer readable medium storing processor executable instructions that, when executed by one or more processors, causes the one or more processors to: (A) receive first read count data, wherein the first read count data was generated by, infecting a first culture of cas9-positive cells with a library of viral vectors, the library comprising at least 3 guide RNAs (gRNAs) for cleaving a target region of DNA within the genome of the cells, and sequencing the cells to obtain a read count for each of the gRNAs; sum ($\Sigma$), based on the first read count data, respective numbers of gRNAs, per target region of DNA, whose read count exceeds a background threshold, wherein $\Sigma$=n; and sum ($\Sigma$), based on the first read count data, a total number of gRNAs, over all target regions, whose read count exceeds the background threshold, wherein $\Sigma$=N; (B) receive second read count data, wherein the second read count data was generated by, infecting a second culture of cas9-positive cells with the library of viral vectors, categorizing the cells of the second culture as either having a designated phenotype or not having the designated phenotype, and selecting cells having the designated phenotype and sequencing the selected cells to obtain a post-selection read count for each of the gRNAs; sum ($\Sigma$), based on the second read count data, respective numbers of gRNAs, per target region of DNA, in the selected cells whose post-selection read count exceeds the background threshold, wherein $\Sigma$=n'; and sum ($\Sigma$), based on the second read count data, a total number of gRNAs, over all target regions, of the selected cells whose read count exceeds the threshold, wherein $\Sigma$=N'; (C) calculate, for a target region of DNA, a probability of observing n' gRNAs for the target region in the selected cells by chance according to the formula $$\frac{\binom{n'}{n} \cdot \binom{N'-n'}{N-n}}{\binom{N'}{N}}, \text{ wherein } \binom{x}{y} = \frac{y!}{x!(y-x)!}$$

computes a number of ways of choosing x objects out of y objects; and calculate, for a target region of DNA that comprises a gene, a probability of observing n' or more gRNAs of the gene in the selected cells by chance according to the formula $$\sum_{i=n'}^{n} \frac{\binom{i}{n} \cdot \binom{N'-i}{N-n}}{\binom{N'}{N}}.$$

Embodiment 55. The non-transitory computer readable medium of embodiment 54, wherein the first culture is infected according to a CRISPR technique.

Embodiment 56. The non-transitory computer readable medium of any one of embodiments 54-55, wherein the cas-9 positive cells of the first culture are modified to contain one or more selectable markers.

Embodiment 57. The non-transitory computer readable medium of any one of embodiments 54-56, wherein a target region comprises a gene.

Embodiment 58. The non-transitory computer readable medium of any one of embodiments 54-57, wherein categorizing cells of the second culture as either having the designated phenotype or not having the designated phenotype comprises applying a selection mechanism to the second cell culture.

Embodiment 59. The non-transitory computer readable medium of embodiment 58, wherein the selection mechanism comprises one or more of exposing the second cell population to a drug or exposing the second cell population to a substance that identifies protein activity or expression levels.

Embodiment 60. The non-transitory computer readable medium of any one of embodiments 54-59, wherein selecting cells having the designated phenotype comprises sorting the cells based on the one or more selectable markers.

Embodiment 61. The non-transitory computer readable medium of any one of embodiments 54-60, further comprising identifying, based on the probability of observing n' or more gRNAs of the gene in the selected cells by chance, that the target region is positively selected.

Embodiment 62. The non-transitory computer readable medium of embodiment 61, wherein identifying that the target region is positively selected comprises determining that the probability of observing n' or more gRNAs of the sequence of interest in the selected cells by chance satisfies a threshold.

Embodiment 63. The non-transitory computer readable medium of any one of embodiments 54-62, further comprising determining, for each gRNA, an enrichment score.

Embodiment 64. The non-transitory computer readable medium of embodiment 63, wherein determining, for each gRNA, the enrichment score comprises evaluating N/N'.

Embodiment 65. The non-transitory computer readable medium of any one of embodiments 54-64, wherein the cas-9 positive cells comprise deactivated cas-9.

Embodiment 66. The non-transitory computer readable medium of embodiment 65, wherein the deactivated cas-9 is fused to at least one transcription activation domain.

Embodiment 67. An apparatus comprising: one or more processors; and memory storing processor executable instructions that, when executed by the one or more processors, cause the apparatus to: determine, based on sequencing a first cell population after infection with a vector comprising a library of at least 3 guide RNAs (gRNAs) for each of a plurality of target regions of DNA, a respective number of gRNAs (n) present for each of the plurality of target regions of DNA, whose read count exceeds a background threshold; determine, based on the respective numbers of gRNAs for each of the plurality of target regions of DNA, a total number of gRNAs (N) present in the first cell population, over all target regions of the plurality of target regions of DNA, whose read count exceeds the background threshold; determine, based on sequencing a second cell population after infection with a vector comprising the library of at least 3 gRNAs for each of the plurality of target regions of DNA, a respective number of gRNAs (n') present for each of the plurality of target regions of DNA, whose read count exceeds the background threshold; determine, based on the respective numbers of gRNAs for each of the plurality of target regions of DNA, a total number of gRNAs (N') present in the second cell population over all target regions of the plurality of target regions of DNA whose read count exceeds the background threshold; determine, for each target region of the plurality of target regions, based on n, N, n', and N', a probability of observing n' gRNAs for the target region in the selected cells by chance; determine, for a target region that comprises a sequence of interest, based on the probability of observing n' gRNAs for the target region in the selected cells by chance, a probability of observing n' or more gRNAs of the sequence of interest in the selected cells by chance; and identify, based on the probability of observing n' or more gRNAs of the sequence of interest in the selected cells by chance, that the sequence of interest is positively selected.

Embodiment 68. The apparatus of embodiment 67, wherein the first cell population and the second population comprise cas-9 positive cells.

Embodiment 69. The apparatus of any one of embodiments 67-68, wherein the processor executable instructions that, when executed by the one or more processors, cause the apparatus to determine, based on sequencing a first cell population after infection with a vector comprising a library of at least 3 gRNAs for each of a plurality of target regions of DNA, a respective number of gRNAs (n) present for each of the plurality of target regions of DNA, whose read count exceeds a background threshold, cause the apparatus to: receive first read count data generated by, infecting the first cell population with the library of viral vectors, and sequencing cells of the first cell population to obtain a read count for each of the gRNAs; and count, based on the first read count data, for each of the plurality of target regions of DNA, each gRNA whose read count exceeds the background threshold.

Embodiment 70. The apparatus of embodiment 69, wherein the processor executable instructions that, when executed by the one or more processors, cause the apparatus to determine, based on the respective numbers of gRNAs for each of the plurality of target regions of DNA, a total number of gRNAs (N) present in the first cell population, over all target regions of the plurality of target regions of DNA, whose read count exceeds the background threshold cause the apparatus to count each gRNA present in the first cell population whose read count exceeds the background threshold.

Embodiment 71. The apparatus of any one of embodiments 67-70, wherein the processor executable instructions that, when executed by the one or more processors, cause the apparatus to determine, based on sequencing a second cell population after infection with a vector comprising the library of at least 3 gRNAs for each of the plurality of target regions of DNA, a respective number of gRNAs (n') present for each of the plurality of target regions of DNA, whose read count exceeds the background threshold cause the apparatus to: receive second read count data generated by, categorizing cells of the second cell population as either having a designated phenotype or not having the designated phenotype; selecting cells having the designated phenotype; sequencing the selected cells to obtain a read count for each of the gRNAs; and count, based on the second read count data, for each of the plurality of target regions of DNA, each gRNA whose read count exceeds the background threshold.

Embodiment 72. The apparatus of any one of embodiments 67-71, wherein the processor executable instructions that, when executed by the one or more processors, cause the apparatus to determine, based on the respective numbers of gRNAs for each of the plurality of target regions of DNA, a total number of gRNAs (N') present in the second cell population over all target regions of the plurality of target regions of DNA whose read count exceeds the background threshold cause the apparatus to count each gRNA present in the selected cells of the second cell population whose read count exceeds the background threshold.

Embodiment 73. The apparatus of any one of embodiments 67-72, wherein the processor executable instructions that, when executed by the one or more processors, cause the apparatus to determine, for each target region of the plurality of target regions, based on n, N, n', and N', the probability of observing n' gRNAs for the target region in the selected cells by chance cause the apparatus to evaluate $$\frac{\binom{n'}{n} \cdot \binom{N'-n'}{N-n}}{\binom{N'}{N}}, \text{ wherein } \binom{x}{y} = \frac{y!}{x!(y-x)!}$$

computes a number of ways of choosing x objects out of y objects.

Embodiment 74. The apparatus of any one of embodiments 67-73, wherein the processor executable instructions that, when executed by the one or more processors, cause the apparatus to determine, for a target region that comprises a sequence of interest, based on the probability of observing n' gRNAs for the target region in the selected cells by chance, a probability of observing n' or more gRNAs of the sequence of interest in the selected cells by chance cause the apparatus to evaluate $$\sum_{i=n'}^{n} \frac{\binom{i}{n} \cdot \binom{N'-i}{N-n}}{\binom{N'}{N}}.$$

Embodiment 75. The apparatus of any one of embodiments 67-74, wherein the processor executable instructions that, when executed by the one or more processors, cause the apparatus to identify, based on the probability of observing n' or more gRNAs of the sequence of interest in the selected cells by chance, that the sequence of interest is positively selected cause the apparatus to evaluate determine that the probability of observing n' or more gRNAs of the sequence of interest in the selected cells by chance satisfies a threshold.

Embodiment 76. The apparatus of any one of embodiments 67-76, further comprising processor executable instructions that, when executed by the one or more processors, cause the apparatus to determine, for each gRNA, an enrichment score.

Embodiment 77. The apparatus of embodiment 76, wherein the processor executable instructions that, when executed by the one or more processors, cause the apparatus to determine, for each gRNA, an enrichment score cause the apparatus to evaluate N/N'.

Embodiment 78. The apparatus of any one of embodiments 67-77, wherein the cas-9 positive cells comprise deactivated cas-9.

Embodiment 79. The apparatus of embodiment 78, wherein the deactivated cas-9 is fused to at least one transcription activation domain.

Embodiment 80. A non-transitory computer readable medium for determining a probability of observing one or more guide RNA (gRNA) by chance, the non-transitory computer readable medium storing processor executable instructions that, when executed by one or more processors, causes the one or more processors to: determine, based on sequencing a first cell population after infection with a vector comprising a library of at least 3 guide RNAs (gRNAs) for each of a plurality of target regions of DNA, a respective number of gRNAs (n) present for each of the plurality of target regions of DNA, whose read count exceeds a background threshold; determine, based on the respective numbers of gRNAs for each of the plurality of target regions of DNA, a total number of gRNAs (N) present in the first cell population, over all target regions of the plurality of target regions of DNA, whose read count exceeds the background threshold; determine, based on sequencing a second cell population after infection with a vector comprising the library of at least 3 gRNAs for each of the plurality of target regions of DNA, a respective number of gRNAs (n') present for each of the plurality of target regions of DNA, whose read count exceeds the background threshold; determine, based on the respective numbers of gRNAs for each of the plurality of target regions of DNA, a total number of gRNAs (N') present in the second cell population over all target regions of the plurality of target regions of DNA whose read count exceeds the background threshold; determine, for each target region of the plurality of target regions, based on n, N, n', and N', a probability of observing n' gRNAs for the target region in the selected cells by chance; determine, for a target region that comprises a sequence of interest, based on the probability of observing n' gRNAs for the target region in the selected cells by chance, a probability of observing n' or more gRNAs of the sequence of interest in the selected cells by chance; and
identify, based on the probability of observing n' or more gRNAs of the sequence of interest in the selected cells by chance, that the sequence of interest is positively selected.

Embodiment 81. The non-transitory computer readable medium of embodiment 80, wherein the first cell population and the second population comprise cas-9 positive cells.

Embodiment 82. The non-transitory computer readable medium of any one of embodiments 80-81, wherein the processor executable instructions that, when executed by the one or more processors, cause the apparatus to determine, based on sequencing a first cell population after infection with a vector comprising a library of at least 3 gRNAs for each of a plurality of target regions of DNA, a respective number of gRNAs (n) present for each of the plurality of target regions of DNA, whose read count exceeds a background threshold, cause the one or more processors to: receive first read count data generated by, infecting the first cell population with the library of viral vectors, and sequencing cells of the first cell population to obtain a read count for each of the gRNAs; and count, based on the first read count data, for each of the plurality of target regions of DNA, each gRNA whose read count exceeds the background threshold.

Embodiment 83. The non-transitory computer readable medium of any one of embodiments 80-82, wherein the processor executable instructions that, when executed by the one or more processors, cause the apparatus to determine, based on the respective numbers of gRNAs for each of the plurality of target regions of DNA, a total number of gRNAs (N) present in the first cell population, over all target regions of the plurality of target regions of DNA, whose read count exceeds the background threshold cause the one or more processors to count each gRNA present in the first cell population whose read count exceeds the background threshold.

Embodiment 84. The non-transitory computer readable medium of any one of embodiments 80-83, wherein the processor executable instructions that, when executed by the one or more processors, cause the apparatus to determine, based on sequencing a second cell population after infection with a vector comprising the library of at least 3 gRNAs for each of the plurality of target regions of DNA, a respective number of gRNAs (n') present for each of the plurality of target regions of DNA, whose read count exceeds the background threshold cause the one or more processors to: receive second read count data generated by, categorizing cells of the second cell population as either having a designated phenotype or not having the designated phenotype; selecting cells having the designated phenotype; sequencing the selected cells to obtain a read count for each of the gRNAs; and count, based on the second read count data, for each of the plurality of target regions of DNA, each gRNA whose read count exceeds the background threshold.

Embodiment 85. The non-transitory computer readable medium of any one of embodiments 80-84, wherein the processor executable instructions that, when executed by the one or more processors, cause the apparatus to determine, based on the respective numbers of gRNAs for each of the plurality of target regions of DNA, a total number of gRNAs (N') present in the second cell population over all target regions of the plurality of target regions of DNA whose read count exceeds the background threshold cause the one or more processors to count each gRNA present in the selected cells of the second cell population whose read count exceeds the background threshold.

Embodiment 86. The non-transitory computer readable medium of any one of embodiments 80-85, wherein the processor executable instructions that, when executed by the one or more processors, cause the apparatus to determine, for each target region of the plurality of target regions, based on n, N, n', and N', the probability of observing n' gRNAs for the target region in the selected cells by chance cause the one or more processors to evaluate $$\frac{\binom{n'}{n} \cdot \binom{N'-n'}{N-n}}{\binom{N'}{N}}, \text{ wherein } \binom{x}{y} = \frac{y!}{x!(y-x)!}$$

computes a number of ways of choosing x objects out of y objects.

Embodiment 87. The non-transitory computer readable medium of any one of embodiments 80-86, wherein the processor executable instructions that, when executed by the one or more processors, cause the apparatus to determine, for a target region that comprises a sequence of interest, based on the probability of observing n' gRNAs for the target region in the selected cells by chance, a probability of observing n' or more gRNAs of the sequence of interest in the selected cells by chance cause the one or more processors to evaluate $$\sum_{i=n'}^{n} \frac{\binom{i}{n} \cdot \binom{N'-i}{N-n}}{\binom{N'}{N}}.$$

Embodiment 88. The non-transitory computer readable medium of any one of embodiments 80-87, wherein the processor executable instructions that, when executed by the one or more processors, cause the apparatus to identify, based on the probability of observing n' or more gRNAs of the sequence of interest in the selected cells by chance, that the sequence of interest is positively selected cause the one or more processors to evaluate determine that the probability of observing n' or more gRNAs of the sequence of interest in the selected cells by chance satisfies a threshold.

Embodiment 89. The non-transitory computer readable medium of any one of embodiments 80-88, further comprising processor executable instructions that, when executed by the one or more processors, cause the one or more processors to determine, for each gRNA, an enrichment score.

Embodiment 90. The non-transitory computer readable medium of embodiment 89, wherein the processor executable instructions that, when executed by the one or more processors, cause the apparatus to determine, for each gRNA, an enrichment score comprises cause the one or more processors to evaluate N/N'.

Embodiment 91. The non-transitory computer readable medium of any one of embodiments 80-90, wherein the cas-9 positive cells comprise deactivated cas-9.

Embodiment 92. The non-transitory computer readable medium of embodiment 91, wherein the deactivated cas-9 is fused to at least one transcription activation domain.

Those skilled in the art will recognize, or be able to ascertain using no more than routine experimentation, many equivalents to the specific embodiments of the method and compositions described herein. Such equivalents are intended to be encompassed by the following claims.

We claim:

1. A method comprising:
   (A) infecting a first culture of cas9-positive cells with a library of viral vectors, the library comprising at least 3 guide RNAs (gRNAs) for cleaving a target region of DNA within the genome of the cells;
   sequencing the cells to obtain a read count for each of the gRNAs;
   summing (Σ) respective numbers of gRNAs (n) qualitatively present, per target region of DNA, whose read count exceeds a background threshold; and
   summing (Σ) a total number of gRNAs (N) qualitatively present, over all target regions, whose read count exceeds the background threshold;
   (B) infecting a second culture of cas9-positive cells with the library of viral vectors;
   categorizing, based on applying a selection mechanism to the cells of the second culture, the cells of the second culture as either having a designated phenotype or not having the designated phenotype;
   selecting cells having the designated phenotype and sequencing the selected cells to obtain a post-selection read count for each of the gRNAs;
   summing (Σ) respective numbers of gRNAs (n') qualitatively present, per target region of DNA, in the selected cells whose post-selection read count exceeds the background threshold; and
   summing (Σ) a total number of gRNAs (N') qualitatively present, over all target regions, of the selected cells whose read count exceeds the background threshold;
   (C) calculating, for a target region of DNA, a probability of observing n' gRNAs for the target region in the selected cells by chance according to the formula $$\frac{\binom{n'}{n} \cdot \binom{N'-n'}{N-n}}{\binom{N'}{N}},$$

wherein $$\binom{x}{y} = \frac{y!}{x!(y-x)!}$$

computes a number of ways of choosing x objects out of y objects; and
   calculating, for a target region of DNA that comprises a gene, a probability of observing n' or more gRNAs of the gene in the selected cells by chance according to the formula $$\sum_{i=n'}^{n} \frac{\binom{i}{n} \cdot \binom{N'-i}{N-n}}{\binom{N'}{N}}.$$

2. The method of claim 1, wherein the cas-9 positive cells of the first culture are modified to contain one or more selectable markers.

3. The method of claim 2, wherein the one or more selectable markers comprise a fluorescent marker.

4. The method of claim 3, wherein the fluorescent marker is part of a FRET biosensor.

5. The method of claim 2, wherein the one or more selectable markers is a detectable enzyme.

6. The method of claim 5, wherein the detectable enzyme is β-galactosidase.

7. The method of claim 5, wherein the detectable enzyme is luciferase.

8. The method of claim 1, wherein the designated phenotype is fluorescence.

9. The method of claim 1, wherein the designated phenotype is cell survival.

10. The method of claim 1, wherein a target region comprises a gene.

11. The method of claim 1, wherein the selection mechanism comprises one or more of exposing the second cell population to a drug or exposing the second cell population to a substance that identifies protein activity or expression levels.

12. The method of claim 1, wherein selecting cells having the designated phenotype comprises sorting the cells based on the one or more selectable markers.

13. The method of claim 1, further comprising identifying, based on the probability of observing n' or more gRNAs of the gene in the selected cells by chance, that the target region is positively selected.

14. The method of claim 13, wherein identifying that the target region is positively selected comprises determining that the probability of observing n' or more gRNAs of the sequence of interest in the selected cells by chance satisfies a threshold.

15. The method of claim 1, further comprising determining, for each gRNA, an enrichment score.

16. The method of claim 15, wherein determining, for each gRNA, the enrichment score comprises evaluating N/N'.

17. The method of claim 1, wherein the target region of DNA regulates a downstream gene or protein.

18. The method of claim 17, wherein regulating a downstream gene or protein comprises the activation or inhibition of the downstream gene or protein.

19. The method of claim 1, further comprising identifying, based on the probability of observing n' or more gRNAs of the gene in the selected cells by chance, the target region as a modifier of a second gene.

20. The method of claim 1, further comprising identifying, based on the probability of observing n' or more gRNAs of the gene in the selected cells by chance, the target region as a therapeutic target.

21. The method of claim 1, further comprising identifying, based on the probability of observing n' or more gRNAs of the gene in the selected cells by chance, the target region as correlated with the designated phenotype.

22. The method of claim 1, further comprising identifying, based on the probability of observing n' or more gRNAs of the gene in the selected cells by chance, the target region as exhibiting a protective effect.

23. A method comprising:
(A) infecting a first culture of cas9-positive cells with a library of viral vectors, the library comprising at least 3 guide RNAs (gRNAs) for enhancing transcription of a target region of DNA within the genome of the cells;
sequencing the cells to obtain a read count for each of the gRNAs;
summing ($\Sigma$) respective numbers of gRNAs (n) qualitatively present, per target region of DNA, whose read count exceeds a background threshold; and
summing ($\Sigma$) a total number of gRNAs (N) qualitatively present, over all target regions, whose read count exceeds the background threshold;
(B) infecting a second culture of cas9-positive cells with the library of viral vectors;
categorizing the cells of the second culture as either having a designated phenotype or not having the designated phenotype;
selecting cells having the designated phenotype and sequencing the selected cells to obtain a post-selection read count for each of the gRNAs;
summing ($\Sigma$) respective numbers of gRNAs (n') qualitatively present, per target region of DNA, in the selected cells whose post-selection read count exceeds the background threshold; and
summing ($\Sigma$) a total number of gRNAs (N') qualitatively present, over all target regions, of the selected cells whose read count exceeds the background threshold;
(C) calculating, for a target region of DNA, a probability of observing n' gRNAs for the target region in the selected cells by chance according to the formula $$\frac{\binom{n'}{n} \cdot \binom{N'-n'}{N-n}}{\binom{N'}{N}}, \text{ wherein } \binom{x}{y} = \frac{y!}{x!(y-x)!}$$

computes a number of ways of choosing x objects out of y objects;
calculating, for a target region of DNA that comprises a gene, a probability of observing n' or more gRNAs of the gene in the selected cells by chance according to the formula $$\sum_{i=n'}^{n} \frac{\binom{i}{n} \cdot \binom{N'-i}{N-n}}{\binom{N'}{N}}.$$

and
identifying, based on the probability of observing n' or more gRNAs of the gene in the selected cells by chance, that the target region is positively selected.

* * * * *